United States Patent
Millett et al.

(10) Patent No.: US 12,290,572 B2
(45) Date of Patent: *May 6, 2025

(54) GENE EDITING TO IMPROVE JOINT FUNCTION

(71) Applicant: ORTHOBIO THERAPEUTICS, INC., Edwards, CO (US)

(72) Inventors: Peter J. Millett, Edwards, CO (US); Iain Alasdair Russell, Cambridge (GB); Matthew J. Allen, Swaffham Bulbeck (GB)

(73) Assignee: ORTHOBIO THERAPEUTICS, INC., Vail, CO (US)

( * ) Notice: Subject to any disclaimer, the term of this patent is extended or adjusted under 35 U.S.C. 154(b) by 887 days.

This patent is subject to a terminal disclaimer.

(21) Appl. No.: 17/241,839

(22) Filed: Apr. 27, 2021

(65) Prior Publication Data

US 2021/0261956 A1 Aug. 26, 2021

Related U.S. Application Data

(63) Continuation of application No. 17/166,343, filed on Feb. 3, 2021, now Pat. No. 11,324,838, which is a continuation of application No. 16/916,014, filed on Jun. 29, 2020, now Pat. No. 11,033,590, which is a continuation of application No. PCT/US2020/014139, filed on Jan. 17, 2020.

(60) Provisional application No. 62/794,340, filed on Jan. 18, 2019, provisional application No. 62/894,184, filed on Aug. 30, 2019, provisional application No. 62/914,635, filed on Oct. 14, 2019.

(51) Int. Cl.
| | |
|---|---|
| A61K 48/00 | (2006.01) |
| A61K 9/00 | (2006.01) |
| A61K 9/127 | (2006.01) |
| A61K 35/76 | (2015.01) |
| A61P 19/02 | (2006.01) |
| C12N 9/22 | (2006.01) |
| C12N 15/11 | (2006.01) |
| C12N 15/113 | (2010.01) |
| C12N 15/85 | (2006.01) |
| C12N 15/86 | (2006.01) |

(52) U.S. Cl.
CPC .......... *A61K 48/00* (2013.01); *A61K 48/0075* (2013.01); *A61P 19/02* (2018.01); *C12N 9/22* (2013.01); *C12N 15/11* (2013.01); *C12N 15/1136* (2013.01); *C12N 15/85* (2013.01); *C12N 15/86* (2013.01); *A61K 9/0019* (2013.01); *A61K 9/127* (2013.01); *A61K 35/76* (2013.01); *C12N 2310/20* (2017.05); *C12N 2750/14143* (2013.01)

(58) Field of Classification Search
CPC ..... A61K 48/00; A61K 48/0075; A61P 19/02; C12N 9/22; C12N 15/11; C12N 15/1136; C12N 15/85; C12N 15/86; C12N 2310/20
USPC ..................... 514/44 R; 435/320.1, 325, 455
See application file for complete search history.

(56) References Cited

U.S. PATENT DOCUMENTS

| | | | |
|---|---|---|---|
| 11,033,590 B2 * | 6/2021 | Millett | .................. C12N 15/86 |
| 11,324,838 B2 * | 5/2022 | Millett | ..................... C12N 9/22 |
| 2002/0146700 A1 | 10/2002 | Duff et al. | |
| 2005/0282198 A1 | 12/2005 | Duff et al. | |
| 2006/0078542 A1 | 12/2006 | Mah et al. | |
| 2009/0019558 A1 | 1/2009 | Song et al. | |
| 2009/0291081 A1 | 11/2009 | Hsieh et al. | |
| 2014/0080782 A1 | 3/2014 | Palmon et al. | |
| 2016/0279202 A1 | 9/2016 | Kamari et al. | |
| 2017/0056448 A1 | 3/2017 | Glick et al. | |
| 2017/0166903 A1 | 6/2017 | Zhang et al. | |
| 2017/0175142 A1 | 6/2017 | Zhang et al. | |
| 2017/0321214 A1 | 11/2017 | Zhang et al. | |
| 2017/0335331 A1 | 11/2017 | Zhao et al. | |
| 2018/0155436 A1 | 6/2018 | Orengo et al. | |
| 2018/0201951 A1 | 7/2018 | Guilak et al. | |
| 2019/0264193 A1 | 8/2019 | Eshghi et al. | |

FOREIGN PATENT DOCUMENTS

| | | |
|---|---|---|
| CN | 108697813 | 10/2018 |
| WO | 2005021768 A1 | 3/2005 |
| WO | 2009114724 | 9/2009 |
| WO | 2017083722 | 5/2017 |
| WO | 2017123934 | 7/2017 |
| WO | 2017223107 A1 | 12/2017 |
| WO | 2018009939 A1 | 1/2018 |
| WO | 2020080979 A1 | 4/2020 |
| WO | 2020150633 | 7/2020 |
| WO | 2022020785 A2 | 1/2022 |

OTHER PUBLICATIONS

Abramson et al. (2002) Rheumatology, vol. 41, 972-980.*
Frisbie et al. (2002) Gene Ther., vol. 9, 12-20.*
Soller et al. (2007) J. Heredity, vol. 98(5), 485-490.*

(Continued)

*Primary Examiner* — Anne Marie S Wehbe
(74) *Attorney, Agent, or Firm* — Morgan, Lewis & Bockius LLP

(57) ABSTRACT

The present invention provides compositions and methods for treating joint disorders that are characterized by an inflammatory component. In some aspects, the compositions and methods are to prevent the progression of osteoarthritis and other arthritides and to treat osteoarthritis and other arthritides in a mammalian joint.

20 Claims, 7 Drawing Sheets

Specification includes a Sequence Listing.

(56) References Cited

OTHER PUBLICATIONS

Ran et al. (2015) Nature, vol. 520, 186-191, and extended data.*
Horai et al. (1998) J Exp Med, vol. 187, p. 1463-1475.*
Daniels et al. (2017) Scientific Reports, vol. 7, 17077, DOI:10.1038/s41598-017-17387-x, pp. 1-12.*
Lau et al. (2017) F1000Research 2017, 6(F1000 Faculty Rev):2153, pp. 1-21, (doi:10.12688/f1000research. 11243.1).*
International Search Report and Written Opinion dated Jun. 16, 2020 for International Patent Application No. PCT/US2020/014139, 13 pages.
Daniels et al., CRISPR/Cas9 mediated mutation of mouse IL-1alpha nuclear localisation sequence abolishes expression, Scientific Reports, Dec. 6, 2017, vol. 7, No. 17077, p. 1-12; abstract; p. 1, para 3, p. 2, para 2.
Wu et al. (2014) Quant. Biol., vol. 2(2), 59-70.
Hsu et al. (2013) Nat. Biotech., vol. 31(9), 827-834.
Fu et al. (2013) Nat. Biotech., vol. 31(9), 822-827.
Karakasheva et al. (2018) Cancer Res., vol. 78 (17), 4957-4970, published online Jul. 5, 2018.
Lau et al. (2017) F1000Resarch 2017, 6(F1000 Faculty Rev):2153, pp. 1-21 (doi: 10.12688/1000research.11243.1).
Horai et al. (1998) J Exp Med, vol. 187, pp. 1463-1475.
Orlinsku et al, (2017) Mol. Ther.:Methods & Clinical Development, vol. 5 , pp. 153-164.
Gopallapa (2018) Nuc. Acid. Res., vol. 46(12), e71, pp. 1-12, published online Mar. 23, 2018.
International Search Report and Written Opinion dated Feb. 2, 2022 for International Patent Application No. PCT/US2021/042100, 22 pages.
International Search Report and Written Opinion dated Feb. 2, 2022 for International Patent Application No. PCT/US2021/043081, 18 pages.
(Klarer, AC et al.) Inhibiti on of 6-phosphofructo-2-kinase {PFKFB3) induces autophagy as a survival mechanism. Cancer and Metabolism. Jan. 23, 2014, vol. 2, No. 2; pp. 1-3; p. 2, 2nd col. 1st paragraph; fig. 1 H: DOI: 10.1186/2049-3002-2-2.
(Pitsillides, AA et al.) The effect of menadione epoxide on the experimental immune arthritis in the rabbit. International Journal of Experimental Pathology. Jun. 1991, vol. 72, No. 3; pp. 301-309; abstract; p. 302, 1st col. 2nd paragraph; table 2; PMID: 1843258.
(Zhao, L et al.) Exploration of CRISPR/Cas9-based gene editing as therapy for osteoarthritis. Annals of Rheumatic Diseases. May 2019, Epub Mar. 6, 2019, vol. 78, No. 5; pp. 676-677; abstract; p. 677, 1st col. 1st paragraph; DOI: 10.1136/annrheumdis-2018-214724 .
(Lepetsos, Pet al.) ROS/oxidative stress signaling in osteoarthritis. Biochimica et Biophysica Acta. Apr. 2016, Epub Jan. 1, 2016. vol. 1862, No. 4; pp. 576-591; entire document; DOI: 10.1016/j.bbadis.2016.01.003.
International Search Report and Written Opinion dated Feb. 3, 2022 for International Patent Application No. PCT/US2021/042048, 22 pages.
International Preliminary Report on Patentability dated Jun. 16, 2021 for International Patent Application No. PCT/US2020/014139, 8 pages.
Daniels et al., CRISPR/Cas9 mediated mutation of mouse IL-1alpha nuclear localisation sequence abolishes expression, Scientific Reports, Dec. 6, 2017, vol. 7, No. 17077, p. 1-12.
Morgan et al., "Crosstalk of reactive oxygen species and NF-B signaling" 103-115. Cell Research (2011) 21 : 103-115.
International Search Report and Written Opinion dated Sep. 19, 2023 for International Patent Application No. PCT/US2023/061407, 14 pages.
International Search Report and Written Opinion dated Jan. 10, 2023 for International Patent Application No. PCT/US2022/037490, 12 pages.
Extended European Search Report and Written Opinion for EP Application No. 20741448.3 dated Oct. 13, 2022, 7 pages.
First Office Action and Search Results for corresponding CN Application No. 202080019618.6 dated Dec. 8, 2023, 9 pages.
Second Office Action issued for CN 202080019618.6 dated Nov. 1, 2024, 15 pages including English translation.

* cited by examiner

GENE EDITING TO IMPROVE JOINT FUNCTION

CROSS-REFERENCE TO RELATED APPLICATIONS

This application is a continuation application of U.S. patent application Ser. No. 17/166,343, filed on Feb. 3, 2021, which is a continuation of U.S. patent application Ser. No. 16/916,014, filed on Jun. 29, 2020, which is a continuation application of International Application No. PCT/US2020/014139, filed on Jan. 17, 2020, which claims priority to Provisional Patent Application No. 62/794,340, filed on Jan. 18, 2019, U.S. Provisional Patent Application No. 62/894,184, filed on Aug. 30, 2019, and U.S. Provisional Patent Application No. 62/914,635, filed on Oct. 14, 2019, each of which are hereby incorporated by reference in their entirety.

FIELD OF THE INVENTION

Compositions and Methods for treating synovial joint dysfunction are described herein. In addition, methods for gene-editing synovial cells and/or synoviocytes, chondrocytes, synovial macrophages, and synovial fibroblasts, and uses of gene-edited synovial cells and/or synoviocytes, chondrocytes, synovial macrophages, and synovial fibroblasts, in the treatment of diseases such as osteoarthritis are disclosed herein.

BACKGROUND OF THE INVENTION

Treatment of osteoarthritis, degenerative joint disease, and other joint dysfunction is complex and there are few long term options for either symptomatic relief or restoring joint function. Osteoarthritis (OA) is the leading cause of disability due to pain. Neogi, *Osteoarthritis Cartilage* 2013; 21:1145-53. All mammal species are affected: working animals, domestic pets, and their owners all suffer OA-related discomfort, pain, and disability, depending on the degree of disease progression.

OA is a complex disease characterized by a progressive course of disability. Systemic inflammation is associated with OA and with OA disease progression. Inflammation is driven by increased levels of pro-inflammatory cytokines. New methods and compositions to treat this disease are acutely needed. Disclosed herein are compositions and methods useful for treating OA as well as other inflammatory joint disorders.

REFERENCE TO A "SEQUENCE LISTING," A TABLE, OR A COMPUTER PROGRAM LISTING APPENDIX SUBMITTED ON A COMPACT DISK

The sequence listing contained in the file named "Sequence Listing 123994-5001-US01.txt" and having a size of 17.1 kilobytes, has been submitted electronically herewith via EFS-Web, and the contents of the .txt file are hereby incorporated by reference in their entirety.

BRIEF SUMMARY OF THE INVENTION

The present invention provides compositions and methods for treating joint disorders that are characterized by an inflammatory component. In some aspects, the compositions and methods are to prevent the progression of osteoarthritis and other arthritides and to treat osteoarthritis and other arthritides in a mammalian joint. According to exemplary embodiments, at least a portion of the joint synovial cells and/or synoviocytes, chondrocytes, synovial macrophages, or synovial fibroblasts are gene-edited to reduce the expression of inflammatory cytokines. In some aspects, at least a portion of the joint synovial cells and/or synoviocytes, chondrocytes, synovial macrophages, or synovial fibroblasts, are gene-edited to reduce the expression of IL-1α, IL-1β, or both IL-1α, IL-1β.

In some embodiments, the gene-editing causes expression of one or more cytokine and/or growth factor genes to be silenced or reduced in at least a portion of the cells comprising a mammalian joint. In some aspects, the cells are synovial cells. In some aspects, the cells are synovial fibroblasts. In some aspects, the cells are synoviocytes. In some aspects, the cells are chondrocytes. In some aspects, the cells are synovial macrophages.

In some embodiments, the one or more cytokine and/or growth factor genes is/are selected from the group comprising IL-1α, and IL-1β.

In some embodiments, the gene-editing comprises the use of a programmable nuclease that mediates the generation of a double-strand or single-strand break at said one or more cytokine and/or growth factor genes.

In some embodiments, the gene-editing comprises one or more methods selected from a CRISPR method, a TALE method, a zinc finger method, and a combination thereof.

In some embodiments, the gene-editing comprises a CRISPR method.

In some embodiments, the CRISPR method is a CRISPR-Cas9 method.

In some embodiments, the gene-editing comprises a TALE method.

In some embodiments, the gene-editing comprises a zinc finger method.

In some embodiments, the gene-editing causes expression of one or more cytokine and/or growth factor genes to be silenced or reduced in at least a portion of the cells comprising the joint. In some embodiments, the portion of cells edited are synoviocytes. In an aspect, the portion of cells edited are synovial fibroblasts. In some embodiments, the portion of cells edited are synoviocytes. In some embodiments, the portion of cells edited are chondrocytes. In some embodiments, the portion of cells edited are synovial macrophages.

In some embodiments, an adeno-associated virus (AAV) delivery system is used to deliver the gene-editing system. In some embodiments, the AAV delivery system is injected into a joint.

Some aspects of the present invention provide a pharmaceutical composition for the treatment or prevention of a joint disease or condition comprising a gene-editing system and a pharmaceutically acceptable carrier. In an aspect, the gene-editing system comprises one or more nucleic acids targeting one or more genetic locus selected from the group consisting of IL-1α, IL-1β, TNF-α, IL-6, IL-8, and IL-18.

An embodiment provides a method of treating canine lameness, the method comprising administering a gene-editing composition, wherein the composition causes expression of IL-1α and IL-1β to be silenced or reduced in a portion of a lame joint's synoviocytes, chondrocytes, synovial macrophages, or synovial fibroblasts.

In some embodiments, the above method further comprises one or more features recited in any of the methods and compositions described herein.

DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIG. 2A: in vivo cleavage of Il1a, edited with 4×sgRNAs (Spy Cas9) in two separate pools (Pool 1 and 2), across two cell lines, NIH 3T3 ("N"), and J774.2 ("J"); FIG. 2B: in vivo cleavage of Il1b, edited with 4×sgRNAs (Spy Cas9) in two separate pools (Pool 1 and 2), across two cell lines, NIH 3T3 ("N"), and J774.2 ("J"); FIG. 2C: in vivo cleavage of Il1a, edited with 3×sgRNAs (Sau Cas9) in two separate pools (Pool 1 and 2), across two cell lines, NIH 3T3 ("N"), and J774.2 ("J"); FIG. 2D: in vivo cleavage of Il1b, edited with 3×sgRNAs (saCas9) in two separate pools (Pool 1 and 2), across two cell lines, NIH 3T3 ("N"), and J774.2 ("J"); editing efficiencies determined using deconvolution of Sanger sequencing traces (ICE tool, Synthego) of each pool.

Figure 1A:
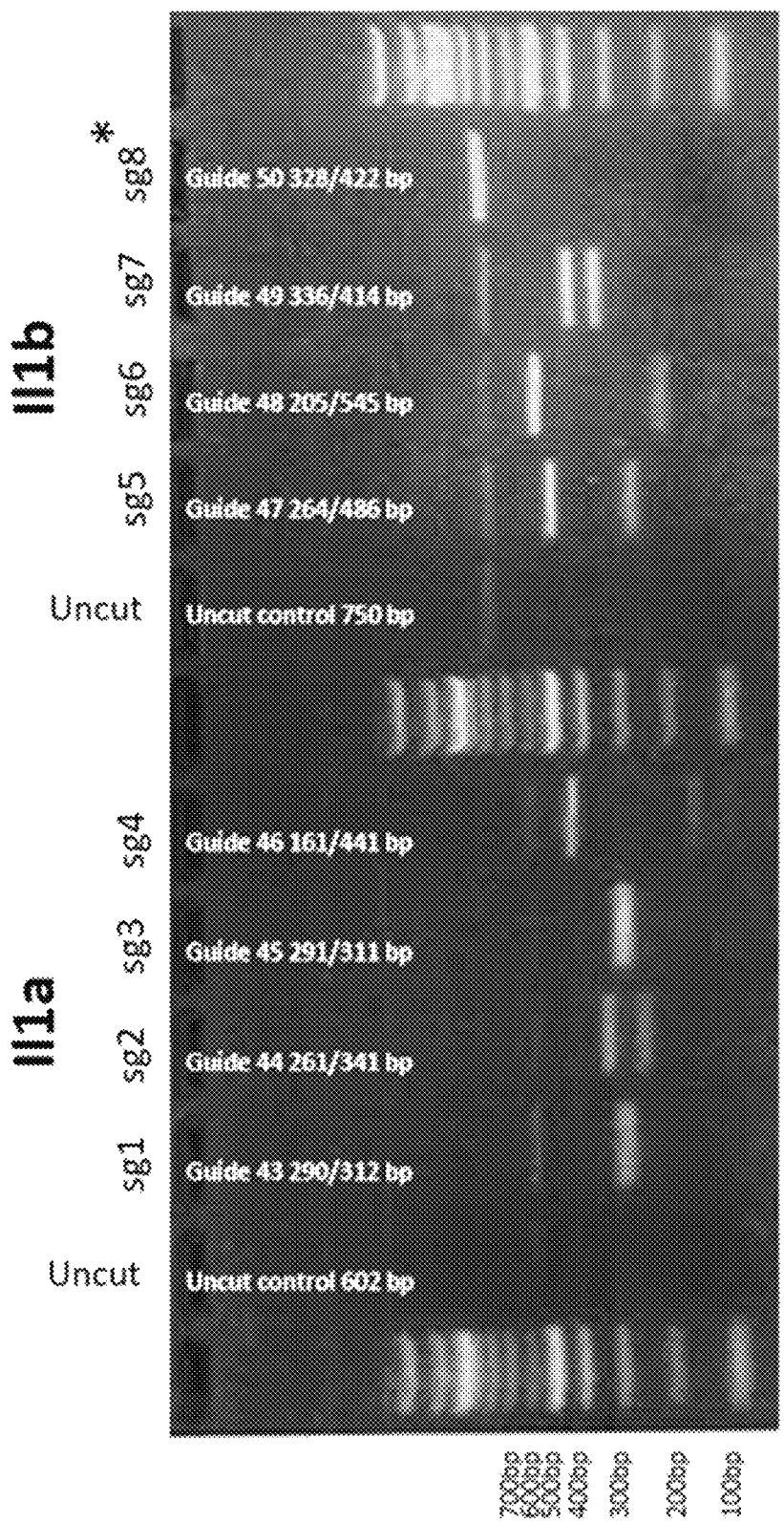
FIG. 1A illustrates an agarose gel electrophoresis analysis of 100 ng mouse DNA (gBlocks, Integrated DNA Technologies) designed against the *Mus musculus* Il1a and Il1b genes, cleaved by 0.5 µg SpyCas9 (TrueCut™ Cas9 protein v2, ThermoFisher Scientific) and 200 ng Phosphorothioate-modified single guide (sg)RNAs targeted against the Il1a gene (#43-46) and Il1b gene (#47-50) in vitro.

While the above-identified drawing sets forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

As described herein, embodiments of the present invention provide compositions and methods for improving joint function and treating joint disease. In particular embodiments, compositions and methods are provided to gene-edit synovial fibroblasts, synoviocytes, chondrocytes, or synovial macrophages to reduce expression of inflammatory cytokines, for example, IL-1α, IL-1β, TNF-α, IL-6, IL-8, IL-18, one or more matrix metalloproteinases (MMPs), or one or more component of the NLRP3 inflammasome. Embodiments are used for treating osteoarthritis and other inflammatory joint diseases. Embodiments are further useful for treating canine lameness due to osteoarthritis. Embodiments are further useful for treating equine lameness due to joint disease. Embodiments are also useful for treating post-traumatic arthritis, gout, pseudogout, and other inflammation-mediated or immune-mediated joint diseases.

Definitions

Unless defined otherwise, all technical and scientific terms used herein have the same meaning as is commonly understood by one of skill in the art to which this invention belongs. All patents and publications referred to herein are incorporated by reference in their entireties.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "ex vivo" refers to an event which involves treating or performing a procedure on a cell, tissue and/or organ which has been removed from a subject's body. Aptly, the cell, tissue and/or organ may be returned to the subject's body in a method of surgery or treatment.

The term "IL-1" (also referred to herein as "IL1") refers to the pro-inflammatory cytokine known as interleukin-1, and includes all forms of IL-1, including IL1-α and IL-1β, human and mammalian forms, conservative amino acid substitutions, glycoforms, biosimilars, and variants thereof. IL-1α and IL-1β bind to the same receptor molecule, which is called type I IL-1 receptor (IL-1RI). There is a third ligand of this receptor: Interleukin 1 receptor antagonist (IL-1Ra), which does not activate downstream signaling; therefore, acting as an inhibitor of IL-1α and IL-1β signaling by competing with them for binding sites of the receptor. See, e.g., Dinarello, *Blood* 117: 3720-32 (2011) and Weber et al., *Science Signaling* 3(105): cm1, doi:10.1126/scisignal.3105 cm1. IL-1 is described, e.g., in Dinarello, *Cytokine Growth Factor Rev.* 8:253-65 (1997), the disclosures of which are incorporated by reference herein. For example, the term IL-1 encompasses human, recombinant forms of IL-1.

TABLE 1

Amino acid sequences of interleukins.

| Identifier | Sequence (One-Letter Amino Acid Symbols) | | | | |
|---|---|---|---|---|---|
| SEQ ID NO: 1 recombinant human IL-1alpha (rhIL-1α) | 10<br>MAKVPDMFED<br>60<br>SVSLSISETS<br>110<br>ANDSEEEIIK<br>160<br>YLTAAALHNL<br>210<br>PVILKEMPEI<br>260<br>WVCLAGGPPS | 20<br>LKNCYSENEE<br>70<br>KTSKLTFKES<br>120<br>PRSAPFSFLS<br>170<br>DEAVKFDMGA<br>220<br>PKTITGSETN<br>270<br>ITDFQILENQ | 30<br>DSSSIDHLSL<br>80<br>MVVVATNGKV<br>130<br>NVKYNFMRII<br>180<br>YKSSKDDAKI<br>230<br>LLFFWETHGT<br>A | 40<br>NQKSFYHVSY<br>90<br>LKKRRLSLSQ<br>140<br>KYEFILNDAL<br>190<br>TVILRISKTQ<br>240<br>KNYFTSVAHP | 50<br>GPLHEGCMDQ<br>100<br>SITDDDLEAI<br>150<br>NQSIIRANDQ<br>200<br>LYVTAQDEDQ<br>250<br>NLFIATKQDY |

TABLE 1-continued

Amino acid sequences of interleukins.

| Identifier | Sequence (One-Letter Amino Acid Symbols) |
|---|---|
| SEQ ID NO: 2 recombinant human IL-1beta (rhIL-1β) | 10 20 30 40 50<br>MAEVPELASE MMAYYSGNED DLFFEADGPK QMKCSFQDLD LCPLDGGIQL<br>60 70 80 90 100<br>RISDHHYSKG FRQAASVVVA MDKLRKMLVP CPQTFQENDL STFFPFIFEE<br>110 120 130 140 150<br>EPIFFDTWDN EAYVHDAPVR SLNCTLRDSQ QKSLVMSGPY ELKALHLQGQ<br>160 170 180 190 200<br>DMEQQVVFSM SFVQGEESND KIPVALGLKE KNLYLSCVLK DDKPTLQLES<br>210 220 230 240 250<br>VDPKNYPKKK MEKRFVFNKI EINNKLEFES AQFPNWYIST SQAENMPVFL<br>260<br>GGTKGGQDIT DFTMQFVSS |
| SEQ ID NO: 3 recombinant mouse IL-1alpha (rmIL-1α) | 10 20 30 40 50<br>MAKVPDLFED LKNCYSENED YSSAIDHLSL NQKSFYDASY GSLHETCTDQ<br>60 70 80 90 100<br>FVSLRTSETS KMSNFTFKES RVTVSATSSN GKILKKRRLS FSETFTEDDL<br>110 120 130 140 150<br>QSITHDLEET IQPRSAPYTY QSDLRYKLMK LVRQKFVMND SLNQTIYQDV<br>160 170 180 190 200<br>DKHYLSTTWL NDLQQEVKFD MYAYSSGGDD SKYPVTLKIS DSQLFVSAQG<br>210 220 230 240 250<br>EDQPVLLKEL PETPKLITGS ETDLIFFWKS INSKNYFTSA AYPELFIATK<br>260 270<br>EQSRVHLARG LPSMTDFQIS |
| SEQ ID NO: 4 recombinant mouse IL-1beta (rmIL-1β) | 10 20 30 40 50<br>MATVPELNCE MPPFDSDEND LFFEVDGPQK MKGCFQTFDL GCPDESIQLQ<br>60 70 80 90 100<br>ISQQHINKSF RQAVSLIVAV EKLWQLPVSF PWTFQDEDMS TFFSFIFEEE<br>110 120 130 140 150<br>PILCDSWDDD DNLLVCDVPI RQLHYRLRDE QQKSLVLSDP YELKALHLNG<br>160 170 180 190 200<br>QNINQQVIFS MSFVQGEPSN DKIPVALGLK GKNLYLSCVM KDGTPTLQLE<br>210 220 230 240 250<br>SVDPKQYPKK KMEKRFVFNK IEVKSKVEFE SAEFPNWYIS TSQAEHKPVF<br>260<br>LGNNSGQDII DFTMESVSS |
| SEQ ID NO: 5 recombinant human IL-1 receptor antagonist (rhIL-1Ra) | 10 20 30 40 50<br>MEICRGLRSH LITLLLFLFH SETICRPSGR KSSKMQAFRI WDVNQKTFYL<br>60 70 80 90 100<br>RNNQLVAGYL QGPNVNLEEK IDVVPIEPHA LFLGIHGGKM CLSCVKSGDE<br>110 120 130 140 150<br>TRLQLEAVNI TDLSENRKQD KRFAFIRSDS GPTTSFESAA CPGWFLCTAM<br>160 170<br>EADQPVSLTN MPDEGVMVTK FYFQEDE |
| SEQ ID NO: 6 recombinant mouse IL-1 receptor antagonist (rmIL-1Ra) | 10 20 30 40 50<br>MEICWGPYSH LISLLLILLF HSEAACRPSG KRPCKMQAFR IWDINQKTFY<br>60 70 80 90 100<br>LRNNQLIAGY LQGPNIKLEE KIDMVPIDLH SVFLGIHGGK LCLSCAKSGD<br>110 120 130 140 150<br>DIKLQLEEVN ITDLSKNKEE DKRFTFIRSE KGPTTSFESA ACPGWFLCTT<br>160 170<br>LEADRPVSLT NTPEEPLIVT KFYFQEDQ |

The term "NLRP3 inflammasome" refers to the multiprotein complex responsible for the activation of some inflammatory responses. The NMRP3 inflammasome promotes the production of functional pro-inflammatory cytokines, for example, IL-1β and IL-18. Core components of the NLRP3 inflammasome are NLRP3, ASC (apoptosis-associated speck-like protein containing a CARD), and caspase-1, as described by Lee et al., *Lipids Health Dis.* 16:271 (2017) and Groslambert and Py, *J. Inflamm. Res.* 11:359-374 (2018).

The terms "matrix metalloproteinase" and "MMP" are defined to be any one of the members of the matrix metalloproteinase family of zinc-endopeptidaes, for example, as characterized by Fanjul-Fernandez et al., *Biochem. Biophys. Acta* 1803:3-19 (2010). In the art, family members are frequently referred to as archetypical MMPs, gelatinases, matrilysins, and/or furin-activatable MMPs. As used herein, the "matrix metalloproteinase" and "MMP" encompass the entire MMP family, including, but not limited to MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20, MMP-21, MMP-23, MMP-25, MMP-26, MMP-27 and MMP-28.

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, at least one anti-inflammatory compound in combination with a viral vector functionally engineered to deliver a gene-editing nucleic acid as described herein) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "effective amount" or "therapeutically effective amount" refers to that amount of a composition or combination of compositions as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells (e.g., the reduction of platelet adhesion and/or cell migration). The specific dose will vary depending on the particular compositions chosen, the dosing regimen to be followed, whether the composition is administered in combination with other compositions or compounds, timing of administration, the tissue to which it is administered, and the physical delivery system in which the composition is carried.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, canine, feline, or equine, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine. It is understood that compositions and methods of the present invention are applicable to treat all mammals, including, but not limited to human, canine, feline, equine, and bovine subjects.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The terms "sequence identity," "percent identity," and "sequence percent identity" (or synonyms thereof, e.g., "99% identical") in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, Calif.) or MegAlign, available from DNASTAR, are additional publicly available software programs that can be used to align sequences. ClustalW and ClustalX may be used to produce alignments, Larkin et al., *Bioinformatics* 23:2947-2948 (2007); Goujon et al., *Nucleic Acids Research*, 38 Suppl:W 695-9 (2010); and, McWilliam et al., *Nucleic Acids Research* 41(Web Server issue):W 597-600 (2013). One skilled in the art can determine appropriate parameters for maximal alignment by particular alignment software. In certain embodiments, the default parameters of the alignment software are used.

As used herein, the term "variant" encompasses but is not limited to antibodies or fusion proteins which comprise an amino acid sequence which differs from the amino acid sequence of a reference antibody by way of one or more substitutions, deletions and/or additions at certain positions within or adjacent to the amino acid sequence of the reference antibody. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody. The term variant also includes pegylated antibodies or proteins.

"Carrier" or "vehicle" as used herein refer to carrier materials suitable for drug administration. Carriers and vehicles useful herein include any such materials known in the art, e.g., any liquid, gel, solvent, liquid diluent, solubilizer, surfactant, or the like, which is nontoxic and which does not interact with other components of the composition in a deleterious manner.

The phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

The term "pharmaceutically acceptable excipient" is intended to include vehicles and carriers capable of being co-administered with a compound to facilitate the performance of its intended function. The use of such media for pharmaceutically active substances is well known in the art. Examples of such vehicles and carriers include solutions, solvents, dispersion media, delay agents, emulsions and the like. Any other conventional carrier suitable for use with the multi-binding compounds also falls within the scope of the present disclosure.

As used herein, the term "a", "an", or "the" generally is construed to cover both the singular and the plural forms.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that compositions, amounts, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The term "substantially" as used herein can refer to a majority of, or mostly, as in at least about 50%, 60%, 70%, 80%, 90%, 95%, 96%, 97%, 98%, 99%, 99.5%, 99.9%, 99.99%, or at least about 99.999% or more.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of," and "consisting of."

"Joint disease" is defined as measurable abnormalities in the cells or tissues of the joint that could lead to illness, for example, metabolic and molecular derangements triggering anatomical and/or physiological changes in the joint. Including, but not limited to, radiographic detection of joint space narrowing, subchondral sclerosis, subchondral cysts, and osteophyte formation.

"Joint illness" is defined in human subjects as symptoms that drive the subject to seek medical intervention, for example, subject reported pain, stiffness, swelling, or immobility. For non-human mammals, "joint illness" is defined, for example, as lameness, observable changes in gait, weight bearing, allodynia, or exploratory behavior.

As used herein, a sgRNA (single guide RNA) is a RNA, preferably a synthetic RNA, composed of a targeting sequence and scaffold. It is used to guide Cas9 to a specific genomic locus in genome engineering experiments. The sgRNA can be administered or formulated, e.g., as a synthetic RNA, or as a nucleic acid comprising a sequence encoding the gRNA, which is then expressed in the target cells.

As used herein, "Cas9" refers to CRISPR Associated Protein; the Cas9 nuclease is the active enzyme for the Type II CRISPR system. "nCas9" refers to a Cas9 that has one of the two nuclease domains inactivated, i.e., either the RuvC or HNH domain. nCas9 is capable of cleaving only one strand of target DNA (a "nickase").

As used herein, "PAM" refers to a Protospacer Adjacent Motif and is necessary for Cas9 to bind target DNA, and immediately follows the target sequence. The Cas9 can be administered or formulated, e.g., as a protein (e.g., a recombinant protein), or as a nucleic acid comprising a sequence encoding the Cas9 protein, which is then expressed in the target cells.

A subject treated by any of the methods or compositions described herein can be of any age and can be an adult, infant or child. In some cases, the subject is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., without limitation, between 2 and 20 years old, between 20 and 40 years old, or between 40 and 90 years old). The subject can be a human or non-human subject. A particular class of subjects that can benefit from the compositions and methods of the present disclosure include subjects over the age of 40, 50, or 60 years. Another class of subjects that can benefit from the compositions and methods of the present disclosure are subjects that have arthritis (e.g., osteoarthritis).

Any of the compositions disclosed herein can be administered to a non-human subject, such as a laboratory or farm animal. Non-limiting examples of a non-human subject include laboratory or research animals, pets, wild or domestic animals, farm animals, etc., e.g., a dog, a goat, a guinea pig, a hamster, a mouse, a pig, a non-human primate (e.g., a gorilla, an ape, an orangutan, a lemur, a baboon, etc.), a rat, a sheep, a horse, a cow, or the like.

The present invention provides compositions useful for treating joint disorders with an inflammatory component. In some aspects, the compositions are useful to prevent the progression of osteoarthritis and to treat osteoarthritis in a mammalian joint.

In some aspects, the pharmaceutical composition comprises a gene-editing system, wherein the gene-editing system causes expression the at least one genetic locus related to joint function to be silenced or reduced in at least a portion of the cells comprising the joint.

In an aspect, the pharmaceutical composition comprises a gene-editing system, wherein the gene-editing system targets one or more of IL-1α, and IL-1β. In some aspects, the pharmaceutical composition comprises a gene-editing system, wherein the gene-editing system targets one or more of TNF-α, IL-6, IL-8, IL-18, a matrix metalloproteinase (MMP), or components of the NLRP3 inflammasome.

In some aspects, the pharmaceutical composition comprises a gene-editing system, wherein the gene-editing comprises the use of a programmable nuclease that mediates the generation of a double-strand or single-strand break at the at least one locus related to joint function. In some embodiments, the gene-editing system reduces the gene expression of the targeted locus or targeted loci. In some embodiments, the at least one locus related to joint tissue is silenced or reduced in at least a portion of the cells comprising the joint.

In some aspects, the cells comprising the joint are synoviocytes. In some aspects, the cells are synovial macrophages. In some aspects, the cells are synovial fibroblasts. In some aspects at least a portion of the synoviocytes are edited. In some aspects, the cells comprising the joint are chondrocytes.

In an aspect, the pharmaceutical composition targets the one or more cytokine and/or growth factor genes is/are selected from the group comprising IL-1α, IL-1β, TNF-α, IL-6, IL-8, IL-18, a matrix metalloproteinase (MMP), or a component of the NLRP3 inflammasome. In some embodiments, the component of the NLRP3 inflammasome comprises NLRP3, ASC (apoptosis-associated speck-like protein containing a CARD), caspase-1, and combinations thereof.

Pharmaceutical compositions are also provided, wherein the gene-editing causes expression of one or more cytokine and/or growth factor genes to be enhanced in at least a portion of the cells comprising the joint, the cytokine and/or growth factor gene(s) being selected from the group comprising IL-1Ra, TIMP-1, TIMP-2, TIMP-3, TIMP-4, and combinations thereof.

In some embodiments, the pharmaceutical composition provides for gene-editing, wherein the gene-editing comprises the use of a programmable nuclease that mediates the generation of a double-strand or single-strand break at said one or more cytokine and/or growth factor genes. In some embodiments, the gene-editing comprises one or more methods selected from a CRISPR method, a TALE method, a zinc finger method, and a combination thereof.

In an aspect, the gene-editing comprises a CRISPR method. In yet other aspects, the CRISPR method is a CRISPR-Cas9 method. In some aspects, the Cas9 is mutated to enhance function.

Animal Models of Osteoarthritis

Several animal models for osteoarthritis are known to the art. Exemplary nonlimiting animal models are summarized; however, it is understood that various models may be used. Many different species of animals are used to mimic OA, for example, studies have been conducted on mice, rats, rabbits, guinea pigs, dogs, pigs, horses, and even other animals. See, e.g., Kuyinu et al., *J Orthop Surg Res.* 11:19 (2016) (hereinafter "Kuyinu, 2016").

It is understood that the various methods for inducing OA may be used in any mammal. In the mouse, spontaneous, chemically induced, surgically induced, and non-invasive induction are commonly used. E.g., Kuyinu, 2016; Bapat et al., *Clin Transl Med.* 7:36 (2018) (hereinafter "Bapat, 2018"); and Poulet, *Curr Rheumatol Rep* 18:40 (2016). In the horse, osteochondral fragment-exercise model, chemical induction, traumatic induction, and induction through overuse are commonly used. In sheep, surgical induction is most common; in the guinea pig, surgical induction, chemical induction, and spontaneous (Durkin Hartley) methods are frequently used. E.g. Bapat, 2018.

The destabilized medial meniscus (DMM) is frequently used in mice to model posttraumatic osteoarthritis, e.g. Culley et al., *Methods Mol Biol.* 1226:143-73 (2015). The DMM model mimics clinical meniscal injury, a known predisposing factor for the development of human OA, and permits the study of structural and biological changes over the course of the disease. Mice are an attractive model organism, because mouse strains with defined genetic backgrounds may be used. Additionally, knock-out or other genetically manipulated mouse strains may be used to evaluate the importance of various molecular pathways in the response to various OA treatment modalities and regimens. For example, STR/ort mice have features that make the strain particularly susceptible to developing OA, including, increased levels of the inflammatory cytokine IL1β, Bapat et al., *Clin Transl Med.* 7:36 (2018). These mice commonly develop OA in knee, ankle, elbow, and temporomandibular joints, Jaeger et al., *Osteoarthritis Cartilage* 16:607-614 (2008). Other useful mutant strains of mice are known to the skilled artisan, for example, Col9a1(−/−) mice, Allen et al., *Arthritis Rheum,* 60:2684-2693 (2009).

Another commonly used surgical model for OA is anterior cruciate ligament transection (ACLT) model. Little and Hunter, *Nat Rev Rheumatol.,* 9(8):485-497 (2013). The subject's ACL is surgically transected causing joint destabilization. The anterior drawer test with the joint flexed is used to confirm that transection of the ligament has occurred. In some cases, other ligaments such as the posterior cruciate ligament, medial collateral ligament, lateral collateral ligament, and/or either meniscus may be transected. As with the DMM model, a variety of mouse strains may be used to investigate various molecular pathways.

Depending on the technical objective, animals of varying size may be selected for use. Rodents are useful because of the short time needed for skeletal maturity and consequently shorter time to develop OA following surgical or other technique to induce OA. Larger animals are particularly useful to evaluate therapeutic interventions. The anatomy in larger animals is very similar to humans; for example, in dogs the cartilage thickness is less than about half the thickness of humans; this striking similarity is exemplary of why such cartilage degeneration and osteochondral defects studies are much more useful in large animal models. E.g. McCoy, *Vet. Pathol.,* 52:803-18 (2015); and, Pelletier et al., *Therapy,* 7:621-34(2010).

Gene-Editing Processes

Overview: Compositions to Gene-Edit Synovial Cells

Embodiments of the present invention are directed to methods for gene-editing synovial cells (synoviocytes), the methods comprising one or more steps of gene-editing at least a portion of the synoviocytes in a joint to treat osteoarthritis or other joint disorder. As used herein, "gene-editing," "gene editing," and "genome editing" refer to a type of genetic modification in which DNA is permanently modified in the genome of a cell, e.g., DNA is inserted, deleted, modified or replaced within the cell's genome. In some embodiments, gene-editing causes the expression of a DNA sequence to be silenced (sometimes referred to as a gene knockout) or inhibited/reduced (sometimes referred to as a gene knockdown). In other embodiments, gene-editing causes the expression of a DNA sequence to be enhanced (e.g., by causing over-expression). In accordance with embodiments of the present invention, gene-editing technology is used to reduce the expression or silence pro-inflammatory genes and/or to enhance the expression of regenerative genes.

Interleukins

According to additional embodiments, gene-editing methods of the present invention may be used to increase the expression of certain interleukins, such as one or more of IL-1α, IL-1β, IL-4, IL-6, IL-8, IL-9, IL-10, IL-13, IL-18, and TNF-α. Certain interleukins have been demonstrated to augment inflammatory responses in joint tissue and are linked to disease progression.

Expression Constructs

Expression constructs encoding one or both of guide RNAs and/or Cas9 editing enzymes can be administered in any effective carrier, e.g., any formulation or composition capable of effectively delivering the component gene to cells in vivo. Approaches include, for example, electroporation and/or insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or CaPO4 precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells. In some instances, the transferred nucleic acids are stably integrated into the chromosomal DNA of the host. In other instances, particularly for adeno-associated virus vectors, stable integration into the host DNA may be a rare event, resulting into episomal expression of the transgene and transient expression of the transgene.

The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, Blood 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., Current Protocols in Molecular Biology, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see, e.g., Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573, each of which is incorporated by reference herein in its entirety for all purposes).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors may be derived from any strain of adenovirus (e.g., Ad2, Ad3, Ad5, or Ad7 etc.), including Adenovirus serotypes from other species (e.g., mouse, dog, human, etc.) that are known to those skilled in the art. The virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Helper-dependent (HDAd) vectors can also be produced with all adenoviral sequences deleted except the origin of DNA replication at each end of the viral DNA along with packaging signal at 5-prime end of the genome downstream of the left packaging signal. HDAd vectors are constructed and propagated in the presence of a replication-competent helper adenovirus that provides the required early and late proteins necessary for replication.

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081

(1985); Wondisford et al., Mol. Endocrinol. 2:32-39 (1988); Tratschin et al., J. Virol. 51:611-619 (1984); and Flotte et al., J. Biol. Chem. 268:3781-3790 (1993). The identification of *Staphylococcus aureus* (SaCas9) and other smaller Cas9 enzymes that can be packaged into adeno-associated viral (AAV) vectors that are highly stable and effective in vivo, easily produced, approved by FDA, and tested in multiple clinical trials, paves new avenues for therapeutic gene editing.

In some embodiments, nucleic acids encoding a CRISPR IL-1α or IL-1β gene editing complex (e.g., Cas9 or gRNA) are entrapped in liposomes bearing positive charges on their surface (e.g., lipofectins), which can be tagged with antibodies against cell surface antigens of the target cells. These delivery vehicles can also be used to deliver Cas9 protein/gRNA complexes.

In clinical settings, the gene delivery systems for the nucleic acids encoding a CRISPR IL-1α or IL-1β gene editing complex can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the nucleic acids encoding a CRISPR IL-1α or IL-1β gene editing complex is more limited, with introduction into the subject being quite localized. For example, the nucleic acids encoding a CRISPR IL-1α or IL-1β gene editing complex can be introduced by intra-articular injection into a joint exhibiting joint disease (e.g., osteoarthritis). In some embodiments, the nucleic acids encoding a CRISPR IL-1α or IL-1β gene editing complex are administered during or after surgery; in some embodiments, a controlled-release hydrogel comprising the nucleic acids encoding a CRISPR IL-1α or IL-1β gene editing complex is administered at the conclusion of surgery before closure to prevent reduce or eliminate osteoarthritis by providing a steady dose of the nucleic acids encoding a CRISPR IL-1α or IL-1β gene editing complex over time.

A pharmaceutical preparation of the nucleic acids encoding a CRISPR IL-1α or IL-1β gene editing complex can consist essentially of the gene delivery system (e.g., viral vector(s)) in an acceptable diluent, or can comprise a slow release matrix in which the gene delivery vehicle is embedded. Alternatively, where the complete gene delivery system can be produced intact from recombinant cells, e.g., adeno-associated viral vectors, the pharmaceutical preparation can comprise one or more cells, which produce the gene delivery system.

Preferably, the CRISPR IL-1α or IL-1β editing complex is specific, i.e., induces genomic alterations preferentially at the target site (IL-1α or IL-1β), and does not induce alterations at other sites, or only rarely induces alterations at other sites. In certain embodiments, the CRISPR IL-1α or IL-1β editing complex has an editing efficiency of at least 50%, at least 60%, at least 70%, at least 80%, at least 90%, at least 95%, or at least 99%. In certain embodiments, the sequence of a guide RNA (e.g., a single guide RNA) may be modified to increase editing efficiency and/or reduce off-target effects. In certain embodiments, the sequence of a guide RNA may vary from the target sequence by about 1 base, about 2 bases, about 3 bases, about 4 bases, about 5 bases, about 5 bases, about 6 bases, about 7 bases, about 8 bases, about 9 bases, about 10 bases, about 15 bases, or greater than about 15 bases. In certain embodiments, the sequence of a guide RNA may vary from the target sequence by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, or greater than about 20%. As used herein, variation form a target sequence may refer to the degree of complementarity.

Gene Editing Methods

As discussed above, embodiments of the present invention provide compositions and methods to treat joint disorders, wherein a portion of the joint cells are genetically modified via gene-editing to treat a joint disorder. Embodiments of the present invention embrace genetic editing through nucleotide insertion (RNA or DNA), or recombinant protein insertion, into a population of synoviocytes for both promotion of the expression of one or more proteins and inhibition of the expression of one or more proteins, as well as combinations thereof. Embodiments of the present invention also provide methods for delivering gene-editing compositions to joint cells, and in particular delivering gene-editing compositions to synoviocytes. There are several gene-editing technologies that may be used to genetically modify joint cells, which are suitable for use in accordance with the present invention.

In some embodiments, a method of genetically modifying joint cells includes the step of stable incorporation of genes for production of one or more proteins. In an embodiment, a method of genetically modifying a portion of a joint's synoviocytes includes the step of retroviral transduction. In an embodiment, a method of genetically modifying a portion of a joint's synoviocytes includes the step of lentiviral transduction. Lentiviral transduction systems are known in the art and are described, e.g., in Levine, et al., Proc. Nat'l Acad. Sci. 2006, 103, 17372-77; Zufferey, et al., Nat. Biotechnol. 1997, 15, 871-75; Dull, et al., J. Virology 1998, 72, 8463-71, and U.S. Pat. No. 6,627,442, the disclosures of each of which are incorporated by reference herein. In an embodiment, a method of genetically modifying a portion of a joint's synoviocytes includes the step of gamma-retroviral transduction. Gamma-retroviral transduction systems are known in the art and are described, e.g., Cepko and Pear, Cur. Prot. Mol. Biol. 1996, 9.9.1-9.9.16, the disclosure of which is incorporated by reference herein. In an embodiment, a method of genetically modifying a portion of a joint's synoviocytes includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tc1-like transposase (SB or Sleeping Beauty transposase), such as SB10, SB11, and SB100x, and engineered enzymes with increased enzymatic activity, are described in, e.g., Hackett, et al., *Mol. Therapy* 2010, 18, 674-83 and U.S. Pat. No. 6,489,458, the disclosures of each of which are incorporated by reference herein.

In some aspects, viral vectors or systems are used to introduce a gene-editing system into cells comprising a joint. In some aspects, the cells are synovial fibroblasts. In some aspects, the viral vectors are an AAV vector. In some aspects, the AAV vector comprises a serotype selected from the group consisting of: AAV1, AAV1(Y705+731F+

T492V), AAV2(Y444+500+730F+T491V), AAV3(Y705+ 731F), AAV4, AAV5, AAV5(Y436+693+719F), AAV6, AAV6 (VP3 variant Y705F/Y731F/T492V), AAV-7m8, AAV8, AAV8(Y733F), AAV9, AAV9 (VP3 variant Y731F), AAV10(Y733F), AAV-ShH10, and AAV-DJ/8. In some aspects, the AAV vector comprises a serotype selected from the group consisting of: AAV1, AAV5, AAV6, AAV6 (Y705F/Y731F/T492V), AAV8, AAV9, and AAV9 (Y731F).

In some aspects, the viral vector is a lentivirus. In an aspect, the lentivirus is selected from the group consisting of: human immunodeficiency-1 (HIV-1), human immunodeficiency-2 (HIV-2), simian immunodeficiency virus (SIV), feline immunodeficiency virus (Hy), bovine immunodeficiency virus (BIV), Jembrana Disease Virus (JDV), equine infectious anemia virus (EIAV), and caprine arthritis encephalitis virus (CAEV).

In an embodiment, a method of genetically modifying a portion of a joint's synoviocytes includes the step of stable incorporation of genes for production or inhibition (e.g., silencing) of one or more proteins. In an embodiment, a method of genetically modifying a portion of a joint's synoviocytes includes the step of liposomal transfection. Liposomal transfection methods, such as methods that employ a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in filtered water, are known in the art and are described in Rose, et al., *Biotechniques* 1991, 10, 520-525 and Felgner, et al., *Proc. Natl. Acad. Sci. USA,* 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In an embodiment, a method of genetically modifying a portion of a joint's synoviocytes includes the step of transfection using methods described in U.S. Pat. Nos. 5,766,902; 6,025,337; 6,410,517; 6,475,994; and 7,189,705; the disclosures of each of which are incorporated by reference herein.

According to an embodiment, the gene-editing process may comprise the use of a programmable nuclease that mediates the generation of a double-strand or single-strand break at one or more immune checkpoint genes. Such programmable nucleases enable precise genome editing by introducing breaks at specific genomic loci, i.e., they rely on the recognition of a specific DNA sequence within the genome to target a nuclease domain to this location and mediate the generation of a double-strand break at the target sequence. A double-strand break in the DNA subsequently recruits endogenous repair machinery to the break site to mediate genome editing by either non-homologous end-joining (NHEJ) or homology-directed repair (HDR). Thus, the repair of the break can result in the introduction of insertion/deletion mutations that disrupt (e.g., silence, repress, or enhance) the target gene product.

Major classes of nucleases that have been developed to enable site-specific genomic editing include zinc finger nucleases (ZFNs), transcription activator-like nucleases (TALENs), and CRISPR-associated nucleases (e.g., CRISPR-Cas9). These nuclease systems can be broadly classified into two categories based on their mode of DNA recognition: ZFNs and TALENs achieve specific DNA binding via protein-DNA interactions, whereas CRISPR systems, such as Cas9, are targeted to specific DNA sequences by a short RNA guide molecule that base-pairs directly with the target DNA and by protein-DNA interactions. See, e.g., Cox et al., *Nature Medicine,* 2015, Vol. 21, No. 2.

Non-limiting examples of gene-editing methods that may be used in accordance with the methods of the present invention include CRISPR methods, TALE methods, and ZFN methods, which are described in more detail below.

CRISPR Methods

A pharmaceutical composition for the treatment or prevention of a joint disease or condition comprising a gene-editing system, wherein said gene-editing system targets at least one locus related to joint function, wherein the gene-editing at least a portion of a joint's synoviocytes by a CRISPR method (e.g., CRISPR-Cas9, CRISPR-Cas13a, or CRISPR/Cpf1 (also known as CRISPR-Cas12a). According to particular embodiments, the use of a CRISPR method to gene-edit joint synoviocytes causes expression of one or more immune checkpoint genes to be silenced or reduced in at least a portion of the joint's synoviocytes.

CRISPR stands for "Clustered Regularly Interspaced Short Palindromic Repeats." A method of using a CRISPR system for gene editing is also referred to herein as a CRISPR method. There are three types of CRISPR systems which incorporate RNAs and Cas proteins, and which may be used in accordance with the present invention: Types II, V, and VI. The Type II CRISPR (exemplified by Cas9) is one of the most well-characterized systems.

CRISPR technology was adapted from the natural defense mechanisms of bacteria and archaea (the domain of single-celled microorganisms). These organisms use CRISPR-derived RNA and various Cas proteins, including Cas9, to foil attacks by viruses and other foreign bodies by chopping up and destroying the DNA, or RNA, of a foreign invader. A CRISPR is a specialized region of DNA with two distinct characteristics: the presence of nucleotide repeats and spacers. Repeated sequences of nucleotides are distributed throughout a CRISPR region with short segments of foreign DNA (spacers) interspersed among the repeated sequences. In the type II CRISPR-Cas system, spacers are integrated within the CRISPR genomic loci and transcribed and processed into short CRISPR RNA (crRNA). These crRNAs anneal to trans-activating crRNAs (tracrRNAs) and direct sequence-specific cleavage and silencing of pathogenic DNA by Cas proteins. Target recognition by the Cas9 protein requires a "seed" sequence within the crRNA and a conserved dinucleotide-containing protospacer adjacent motif (PAM) sequence upstream of the crRNA-binding region. The CRISPR-Cas system can thereby be retargeted to cleave virtually any DNA sequence by redesigning the crRNA. The crRNA and tracrRNA in the native system can be simplified into a single guide RNA (sgRNA) of approximately 100 nucleotides for use in genetic engineering. The CRISPR-Cas system is directly portable to human cells by co-delivery of plasmids expressing the Cas9 endo-nuclease and the necessary crRNA and tracrRNA (or sgRNA) components. Different variants of Cas proteins may be used to reduce targeting limitations (e.g., orthologs of Cas9, such as Cpf1).

Non-limiting examples of genes that may be silenced or inhibited by permanently gene-editing synoviocytes via a CRISPR method include IL-1α, IL-1β, IL-4, IL-9, IL-10, IL-13, and TNF-α.

Non-limiting examples of genes that may be enhanced by permanently gene-editing synoviocytes via a CRISPR method include IL-1α, IL-1β, IL-4, IL-9, IL-10, IL-13, and TNF-α.

Examples of systems, methods, and compositions for altering the expression of a target gene sequence by a CRISPR method, and which may be used in accordance with embodiments of the present invention, are described in U.S. Pat. Nos. 8,697,359; 8,993,233; 8,795,965; 8,771,945; 8,889,356; 8,865,406; 8,999,641; 8,945,839; 8,932,814; 8,871,445; 8,906,616; and 8,895,308, which are incorporated by reference herein. Resources for carrying out CRISPR methods, such as plasmids for expressing CRISPR-Cas9 and CRISPR-Cpf1, are commercially available from companies such as GenScript.

In an embodiment, genetic modifications of at least a portion of a joint's synoviocytes, as described herein, may be performed using the CRISPR-Cpf1 system as described in U.S. Pat. No. 9,790,490, the disclosure of which is incorporated by reference herein.

In an embodiment, genetic modifications of at least a portion of a joint's synoviocytes, as described herein, may be performed using a CRISPR-Cas system comprising single vector systems as described in U.S. Pat. No. 9,907,863, the disclosure of which is incorporated by reference herein.

TALE Methods

A pharmaceutical composition for the treatment or prevention of a joint disease or condition comprising a gene-editing system, wherein said gene-editing system targets at least one locus related to joint function, wherein the method further comprises gene-editing at least a portion of joint synoviocytes by a TALE method. According to particular embodiments, the use of a TALE method to target at least one locus related to joint function, wherein the gene-editing at least a portion of a joint's synoviocytes. Alternatively, the use of a TALE method during to target at least one locus related to joint function, wherein the gene-editing at least a portion of a joint's synoviocytes to cause expression of at least one locus related to joint function genes to be enhanced in at least a portion of the joint synoviocytes.

TALE stands for "Transcription Activator-Like Effector" proteins, which include TALENs ("Transcription Activator-Like Effector Nucleases"). A method of using a TALE system for gene editing may also be referred to herein as a TALE method. TALEs are naturally occurring proteins from the plant pathogenic bacteria genus *Xanthomonas*, and contain DNA-binding domains composed of a series of 33-35-amino-acid repeat domains that each recognizes a single base pair. TALE specificity is determined by two hypervariable amino acids that are known as the repeat-variable di-residues (RVDs). Modular TALE repeats are linked together to recognize contiguous DNA sequences. A specific RVD in the DNA-binding domain recognizes a base in the target locus, providing a structural feature to assemble predictable DNA-binding domains. The DNA binding domains of a TALE are fused to the catalytic domain of a type IIS FokI endonuclease to make a targetable TALE nuclease. To induce site-specific mutation, two individual TALEN arms, separated by a 14-20 base pair spacer region, bring FokI monomers in close proximity to dimerize and produce a targeted double-strand break.

Several large, systematic studies utilizing various assembly methods have indicated that TALE repeats can be combined to recognize virtually any user-defined sequence. Custom-designed TALE arrays are also commercially available through Cellectis Bioresearch (Paris, France), Transposagen Biopharmaceuticals (Lexington, Ky., USA), and Life Technologies (Grand Island, N.Y., USA). TALE and TALEN methods suitable for use in the present invention are described in U.S. Patent Application Publication Nos. US 2011/0201118 A1; US 2013/0117869 A1; US 2013/0315884 A1; US 2015/0203871 A1 and US 2016/0120906 A1, the disclosures of which are incorporated by reference herein.

Non-limiting examples of genes that may be silenced or inhibited by permanently gene-editing synoviocytes via a TALE method include IL-1α, IL-1β, IL-4, IL-9, IL-10, IL-13, and TNF-α.

Non-limiting examples of genes that may be enhanced by permanently gene-editing synoviocytes via a TALE method include IL-1α, IL-1β, IL-4, IL-9, IL-10, IL-13, and TNF-α.

Examples of systems, methods, and compositions for altering the expression of a target gene sequence by a TALE method, and which may be used in accordance with embodiments of the present invention, are described in U.S. Pat. No. 8,586,526, which is incorporated by reference herein.

Zinc Finger Methods

A pharmaceutical composition for the treatment or prevention of a joint disease or condition comprising a gene-editing system, wherein said gene-editing system targets at least one locus related to joint function, wherein the method further comprises gene-editing at least a portion of joint synoviocytes by a zinc finger or zinc finger nuclease method. According to particular embodiments, the use of a zinc finger method to target at least one locus related to joint function, wherein the gene-editing at least a portion of a joint's synoviocytes. Alternatively, the use of a zinc finger method during to target at least one locus related to joint function, wherein the gene-editing at least a portion of a joint's synoviocytes to cause expression of at least one locus related to joint function genes to be enhanced in at least a portion of the joint synoviocytes.

An individual zinc finger contains approximately 30 amino acids in a conserved ββα configuration. Several amino acids on the surface of the α-helix typically contact 3 bp in the major groove of DNA, with varying levels of selectivity. Zinc fingers have two protein domains. The first domain is the DNA binding domain, which includes eukaryotic transcription factors and contain the zinc finger. The second domain is the nuclease domain, which includes the FokI restriction enzyme and is responsible for the catalytic cleavage of DNA.

The DNA-binding domains of individual ZFNs typically contain between three and six individual zinc finger repeats and can each recognize between 9 and 18 base pairs. If the zinc finger domains are specific for their intended target site then even a pair of 3-finger ZFNs that recognize a total of 18 base pairs can, in theory, target a single locus in a mammalian genome. One method to generate new zinc-finger arrays is to combine smaller zinc-finger "modules" of known specificity. The most common modular assembly process involves combining three separate zinc fingers that can each recognize a 3 base pair DNA sequence to generate a 3-finger array that can recognize a 9 base pair target site. Alternatively, selection-based approaches, such as oligomerized pool engineering (OPEN) can be used to select for new zinc-finger arrays from randomized libraries that take into consideration context-dependent interactions between neighboring fingers. Engineered zinc fingers are available commercially; Sangamo Biosciences (Richmond, Calif., USA) has developed a propriety platform (CompoZr®) for zinc-finger construction in partnership with Sigma-Aldrich (St. Louis, Mo., USA).

Non-limiting examples of genes that may be silenced or inhibited by permanently gene-editing synoviocytes via a zinc finger method include IL-1α, IL-1β, IL-4, IL-9, IL-10, IL-13, TNF-α. IL-6, IL-8, IL-18, a matrix metalloproteinase (MMP), or a component of the NLRP3 inflammasome. In some embodiments, the component of the NLRP3 inflammasome comprises NLRP3, ASC (apoptosis-associated speck-like protein containing a CARD), caspase-1, and combinations thereof.

Non-limiting examples of genes that may be enhanced by permanently gene-editing synoviocytes via a zinc finger method include group comprising IL-1Ra, TIMP-1, TIMP- 2, TIMP-3, TIMP-4, and combinations thereof. In an aspect, the invention provides compositions for up-regulation of anti-inflammatory cytokines.

Examples of systems, methods, and compositions for altering the expression of a target gene sequence by a zinc finger method, which may be used in accordance with embodiments of the present invention, are described in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, which are incorporated by reference herein.

In some aspects, cells may be gene-edited ex vivo, wherein the gene-editing targets one or more anti-inflammatory cytokine locus. In some aspects, the cells are non-synovial cells. In some aspects, the cells are mesenchymal stem cells. In some aspect, the cells are macrophages. In some aspects, the present invention provides for a pharmaceutical composition for the treatment or prevention of a joint disease or condition comprising a population of gene-edited cells, wherein said gene-edited cells are edited by a gene-editing system targeting at least one locus related to joint function. In an aspect, the population of gene-edited cells are injected into a synovial joint.

Other examples of systems, methods, and compositions for altering the expression of a target gene sequence by a zinc finger method, which may be used in accordance with embodiments of the present invention, are described in Beane, et al., *Mol. Therapy*, 2015, 23 1380-1390, the disclosure of which is incorporated by reference herein.

Methods of Treating Osteoarthritis and Other Diseases

The compositions and methods described herein can be used in a method for treating diseases. In an embodiment, they are for use in treating inflammatory joint disorders. They may also be used in treating other disorders as described herein and in the following paragraphs. In an aspect, the compositions and methods are used to treat osteoarthritis (OA).

In some embodiments, the present disclosure provides a method for the treatment or prevention of a joint disease or condition the method comprising introducing a gene-editing system, wherein the gene-editing system targets at least one locus related to joint function. In some embodiments, the joint disease is osteoarthritis. In an aspect, the method is used to treat a canine with osteoarthritis. In another aspect, the method is used to treat a mammal with degenerative joint disease. In some aspects, the method is used to treat a canine or an equine with a joint disease. In some aspects, the method is used to treat osteoarthritis, post-traumatic arthritis, post-infectious arthritis, rheumatoid arthritis, gout, pseudogout, auto-immune mediated arthritides, inflammatory arthritides, inflammation-mediated and immune-mediated diseases of joints.

In some embodiments, the method further comprises gene-editing a portion of a the joint synoviocytes to reduce or silence the expression of one or more of IL-1α, IL-1β, IL-4, IL-9, IL-10, IL-13, and TNF-α. In an aspect, the method further comprises gene-editing a portion of a the joint synoviocytes to reduce or silence the expression of one or more of IL-1α, IL-1β.

In an aspect, the method further comprises gene-editing, wherein the gene-editing comprises one or more methods selected from a CRISPR method, a TALE method, a zinc finger method, and a combination thereof.

In some aspects, the method further comprises delivering the gene-editing using an AAV vector, a lentiviral vector, or a retroviral vector. In a preferred embodiment, the method further comprises delivering the gene-editing using AAV1, AAV1(Y705+731F+T492V), AAV2(Y444+500+730F+T491V), AAV3(Y705+731F), AAV5, AAV5(Y436+693+719F), AAV6, AAV6 (VP3 variant Y705F/Y731F/T492V), AAV-7m8, AAV8, AAV8(Y733F), AAV9, AAV9 (VP3 variant Y731F), AAV10(Y733F), and AAV-ShH10. In some aspects, the AAV vector comprises a serotype selected from the group consisting of: AAV1, AAV5, AAV6, AAV6 (Y705F/Y731F/T492V), AAV8, AAV9, and AAV9 (Y731F).

Pharmaceutical Compositions and Methods of Administration

The methods described herein include the use of pharmaceutical compositions comprising CRISPR gene (e.g., IL-1α and/or IL-1β) editing complexes as an active ingredient.

Depending on the method/route of administration, pharmaceutical dosage forms come in several types. These include many kinds of liquid, solid, and semisolid dosage forms. Common pharmaceutical dosage forms include pill, tablet, or capsule, drink or syrup, and natural or herbal form such as plant or food of sorts, among many others. Notably, the route of administration (ROA) for drug delivery is dependent on the dosage form of the substance in question. A liquid pharmaceutical dosage form is the liquid form of a dose of a chemical compound used as a drug or medication intended for administration or consumption.

In one embodiment, a composition of the present disclosure can be delivered to a subject subcutaneously (e.g., intra-articular injection), dermally (e.g., transdermally via patch), and/or via implant. Exemplary pharmaceutical dosage forms include, e.g., pills, osmotic delivery systems, elixirs, emulsions, hydrogels, suspensions, syrups, capsules, tablets, orally dissolving tablets (ODTs), gel capsules, thin films, adhesive topical patches, lollipops, lozenges, chewing gum, dry powder inhalers (DPIs), vaporizers, nebulizers, metered dose inhalers (MDIs), ointments, transdermal patches, intradermal implants, subcutaneous implants, and transdermal implants.

As used herein, "dermal delivery" or "dermal administration" can refer to a route of administration wherein the pharmaceutical dosage form is taken to, or through, the dermis (i.e., layer of skin between the epidermis (with which it makes up the cutis) and subcutaneous tissues). "Subcutaneous delivery" can refer to a route of administration wherein the pharmaceutical dosage form is to or beneath the subcutaneous tissue layer.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

Therapeutic compounds can be prepared with carriers that will protect the therapeutic compounds against rapid elimination from the body, such as a controlled release formulation, including implants and microencapsulated delivery systems. Biodegradable, biocompatible polymers can be used, such as collagen, ethylene vinyl acetate, polyanhydrides (e.g., poly[1,3-bis(carboxyphenoxy)propane-co-sebacic-acid] (PCPP-SA) matrix, fatty acid dimer-sebacic acid (FAD-SA) copolymer, poly(lactide-co-glycolide)), polyglycolic acid, collagen, polyorthoesters, polyethyleneglycol-coated liposomes, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811. Semisolid, gelling, soft-gel, or other formulations (including controlled release) can be used, e.g., when administration to a surgical site is desired. Methods of making such formulations are known in the art and can include the use of biodegradable, biocompatible polymers. See, e.g., Sawyer et al., Yale J Biol Med. 2006 December; 79(3-4): 141-152.

The pharmaceutical compositions can be included in a container, kit, pack, or dispenser together with instructions for administration.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1. Reducing IL-1 Expression by CRISPR Gene-Engineering in a Mouse Model of Osteoarthritis Sixty C57B mice are selected and distributed into four groups of fifteen mice each. The DMM surgical method is used to induce OA in each of the mice. Once the mice have developed OA, the mice are treated as follows:

Group 1: Direct injection into the OA joint a CRISPR AAV vector engineered to target IL-1α and IL-1β, and silence or reduce the expression of IL-1 protein.

Group 2: Direct injection into the OA joint a CRISPR AAV vector engineered with a "nonsense" payload that will not affect an IL-1 production; a negative control.

Group 3: Direct injection into the OA joint a CRISPR AAV vector engineered to target IL-1Ra, and silence or reduce the expression of IL-1Ra protein.

Group 4: Direct injection into the OA joint sterile buffered saline; a control for the injection process.

The mice are monitored before and after treatment to assess effects on their locomotion, and exploratory activities. Mechanical sensitivity and changes to the gait are also monitored. Allodynia and hind limb grip force may also be monitored.

After about eight weeks, the animals are sacrificed and the OA joint tissue assessed for gross histopathology, and IL-1 expression by IHC. Biomarkers of inflammation are also assessed, for example, MMP-3 expression in the OA joint.

Group 1 mice, treated with a CRISPR AAV vector engineered to target IL-1α and IL-1β, and silence or reduce the expression of IL-1 protein, will show reduced levels of IL-1 by IHC, tissue regeneration by histopathology, and lower levels of inflammation biomarkers than any of the three other Groups. Group 3 mice will show relatively higher levels of inflammation biomarker than any of the other three groups.

Example 2. Assessing Guide Cutting Efficiency Against Mouse IL1A and IL1B

In Vitro Cleavage Assay

CRISPR guide RNA's (Phosphorothionate-modified sgRNA, Table 3) were designed against Exon 4 of Il1a and Exon 4 of Il1b (Il1a-201 ENSMUST00000028882.1 and Il1b-201 ENSMUST00000028881.13; see Table 2 for target sequences on Exon 4 of Il1a and Exon 4 of Il1b). C57BL/6 mouse genomic DNA was used to amplify Exon 4 of Il1a and Il1b by PCR (Phusion High-Fidelity DNA polymerase, NEB cat #M0530S) Il1a primer fwd: CATTGGGAG-GATGCTTAGGA, Il1a primer rev: GGCTGCTTTCTCTC-CAACAG, Il1b primer fwd: AGGAAGCCTGTGTCTGGTTG, Il1b primer rev: TGG-CATCGTGAGATAAGCTG. Amplicons were PCR purified (QiaQuick PCR purification kit cat #28106). Guide cutting efficiency was determined using an in vitro cleavage assay using 100 ng purified PCR product, 200 ng modified guide RNA (Sigma Aldrich) and 0.5 μg TrueCut Spy Cas9 protein V2 (Invitrogen A36498) or 0.5 μg Gene Snipper NLS Sau Cas9 (BioVision Cat #M1281-50-1). The two types of Cas9, S. pyogenes Cas9 and S. aureus Cas9, were compared for their editing capabilities. A 2% agarose gel was used for a qualitative readout of the cleavage assay.

Editing Cell Lines

CRISPR guide RNA's (Phosphorothionate-modified sgRNA, Table 2) were designed against Exon 4 of Il1a and Exon 4 of Il1b (Il1a-201 ENSMUST00000028882.1 and Il1b-201 ENSMUST00000028881.13). Guide RNA cutting efficiency was determined in a pool of J774.2 and NIH3T3 cells using Sanger sequencing and Synthego ICE (see, e.g., Inference of CRISPR Edits from Sanger Trace Data, Hsiau T, Maures T, Waite K, Yang J et al. biorxiv. 2018, which is incorporated by reference herein for all purposes), or TIDE (see, e.g., Easy quantitative assessment of genome editing by sequence trace decomposition, Brinkman E, Chen T, Amendola M and Van Steensel B. Nucleic Acids res 2014, which is incorporated by reference herein for all purposes) web tools to calculate percent editing. The experiment also compared the efficiency of S. pyogenes Cas9 and S. aureus Cas9. The cells were electroporated (Amaxa 4D Nucleofector unit, Lonza) with 5 μg TrueCut Spy Cas9 protein V2 (Invitrogen A36498) or 5 μg EnGen Sau Cas9 protein (NEB M0654T) with 100 pmol modified guide RNA (Sigma Aldrich). SF nucleofector solution and programme CM139 was used for J774.2 cells and SG nucleofector solution and programme EN158 was used for NIH3T3 cells. A cell pellet was taken 3 days' post electroporation and gDNA was extracted from each pool (Qiagen, DNeasy blood and tissue kit, 69506). Exon 4 of Il1a or Il1b was amplified in the appropriate pool by PCR (Phusion High-Fidelity DNA polymerase, NEB, cat #M0530S). Il1a primer fwd: TGGTTTCAGGAAAACCCAAG, Il1a primer rev: GCAGTATGGCCAAGAAAGGA, Il1b primer fwd: AGGAAGCCTGTGTCTGGTTG, Il1b primer rev: CTGGGCAAGAACATTGGATT. Amplicons were subjected to Sanger sequencing, and analyzed using either the Synthego ICE or TIDE web tools to determine the absence of wild type sequence in each clone and the presence of indels resulting in a frameshift in the cDNA sequence.

TABLE 2

Target Il1a and Il1b Sequences

| Identifier | Guide ID | Gene | Exon | Cas9 | Target Sequence 5'-3' | PAM |
|---|---|---|---|---|---|---|
| SEQ ID NO: 7 | sg43 | Il1a | 4 | S.pyogenes | GTATCAGCAACGTCAAGCAA | CGG |
| SEQ ID NO: 8 | sg44 | Il1a | 4 | S.pyogenes | CTGCAGGTCATCTTCAGTGA | AGG |
| SEQ ID NO: 9 | sg45 | Il1a | 4 | S.pyogenes | TATCAGCAACGTCAAGCAAC | GGG |
| SEQ ID NO: 10 | sg46 | Il1a | 4 | S.pyogenes | GCCATAGCTTGCATCATAGA | AGG |
| SEQ ID NO: 11 | sg47 | Il1b | 4 | S.pyogenes | CATCAACAAGAGCTTCAGGC | AGG |
| SEQ ID NO: 12 | sg48 | Il1b | 4 | S.pyogenes | TGCTCTCATCAGGACAGCCC | AGG |
| SEQ ID NO: 13 | sg49 | Il1b | 4 | S.pyogenes | GCTCATGTCCTCATCCTGGA | AGG |
| SEQ ID NO: 14 | sg50 | Il1b | 4 | S.pyogenes | CCTCATCCTGGAAGGTCCAC | GGG |
| SEQ ID NO: 15 | sg51 | Il1a | 4 | S.aureus | TTACTCCTTACCTTCCAGATC | ATGGGT |
| SEQ ID NO: 16 | sg52 | Il1a | 4 | S.aureus | GAAACTCAGCCGTCTCTTCTT | CAGAAT |
| SEQ ID NO: 17 | sg53 | Il1a | 4 | S.aureus | CAACTTCACCTTCAAGGAGAG | CCGGGT |
| SEQ ID NO: 18 | sg54 | Il1b | 4 | S.aureus | GTGTCTTTCCCGTGGACCTTC | CAGGAT |

TABLE 2-continued

Target Il1a and Il1b Sequences

| Identifier | Guide ID | Gene | Exon | Cas9 | Target Sequence 5'-3' | PAM |
|---|---|---|---|---|---|---|
| SEQ ID NO: 19 | sg55 | Il1b | 4 | S.aureus | CACAGCTTCTCCACAGCCACA | AGTAGT |
| SEQ ID NO: 20 | sg56 | Il1b | 4 | S.aureus | GTGCTGCTGCGAGATTTGAAG | CTGGAT |

TABLE 3

CRISPR Guide RNA's.

| Identifier | Guide ID | Gene | Exon | Cas9 | cRNA Sequence 5'-3' | PAM |
|---|---|---|---|---|---|---|
| SEQ ID NO: 21 | sg43 | Il1a | 4 | S.pyogenes | GUAUCAGCAACGUCAAGCAA | CGG |
| SEQ ID NO: 22 | sg44 | Il1a | 4 | S.pyogenes | CUGCAGGUCAUCUUCAGUGA | AGG |
| SEQ ID NO: 23 | sg45 | Il1a | 4 | S.pyogenes | UAUCAGCAACGUCAAGCAAC | GGG |
| SEQ ID NO: 24 | sg46 | Il1a | 4 | S.pyogenes | GCCAUAGCUUGCAUCAUAGA | AGG |
| SEQ ID NO: 25 | sg47 | Il1b | 4 | S.pyogenes | CAUCAACAAGAGCUUCAGGC | AGG |
| SEQ ID NO: 26 | sg48 | Il1b | 4 | S.pyogenes | UGCUCUCAUCAGGACAGCCC | AGG |
| SEQ ID NO: 27 | sg49 | Il1b | 4 | S.pyogenes | GCUCAUGUCCUCAUCCUGGA | AGG |
| SEQ ID NO: 28 | sg50 | Il1b | 4 | S.pyogenes | CCUCAUCCUGGAAGGUCCAC | GGG |
| SEQ ID NO: 29 | sg51 | Il1a | 4 | S.aureus | UUACUCCUUACCUUCCAGAUC | ATGGGT |
| SEQ ID NO: 30 | sg52 | Il1a | 4 | S.aureus | GAAACUCAGCCGUCUCUUCUU | CAGAAT |
| SEQ ID NO: 31 | sg53 | Il1a | 4 | S.aureus | CAACUUCACCUUCAAGGAGAG | CCGGGT |
| SEQ ID NO: 32 | sg54 | Il1b | 4 | S.aureus | GUGUCUUUCCCGUGGACCUUC | CAGGAT |
| SEQ ID NO: 33 | sg55 | Il1b | 4 | S.aureus | CACAGCUUCUCCACAGCCACA | AGTAGT |
| SEQ ID NO: 34 | sg56 | Il1b | 4 | S.aureus | GUGCUGCUGCGAGAUUUGAAG | CTGGAT |

Each cRNA (see, e.g., Table 3) was synthesized as a single guide RNA consisting of the cRNA sequences above fused to the tracrRNA sequences below (see, e.g., SEQ ID Nos: 35-36). In certain embodiments, an A< >U flip is used to increase guide RNA activity.

Sau Cas9:

(SEQ ID NO: 35)
GUUAUAGUACUCUGGAAACAGAAUCUACUAAAACAAGGCAAAAUGCCGU
GUUUAUCUCGUCAACUUGUUGGCGAGAUUUUU

Spy Cas9:

(SEQ ID NO: 36)
GUUAUAGAGCUAGAAAUAGCAAGUUAAAAUAAGGCUAGUCCGUUAUCAA
CUUGAAAAAGUGGCACCGAGUCGGUGCUUUUUU

In Vitro Cleavage Assay

FIG. 1A illustrates agarose gel electrophoresis analysis of 100 ng mouse DNA, cleaved by 0.5 μg Spy Cas9 and 200 ng modified guide RNA's 43-46 for Il1a gene and 47-50 for IL1B. DNA is cut at a specific site by the cas9 using the guide RNA to create a predictable band pattern on the agarose gel compared to the uncut control (without wishing to be bound by any particular theory, the agarose gel electrophoresis for sg8* appears to show a failed synthesis).

Figure 1B:
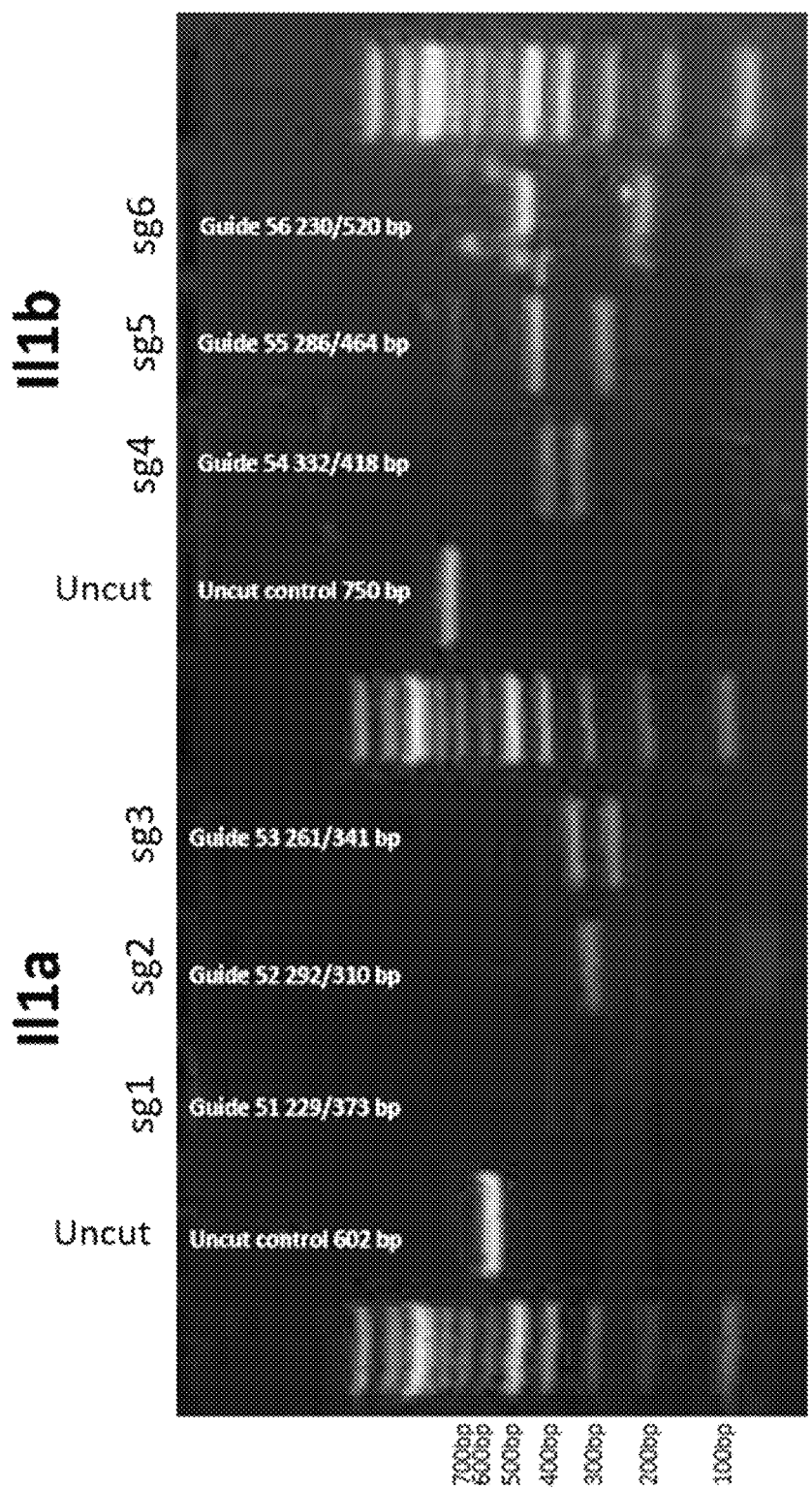
FIG. 1B illustrates an agarose gel electrophoresis analysis of 100 ng mouse DNA (gBlocks, Integrated DNA Technologies) designed against the *Mus musculus* Il1a and Il1b genes, cleaved by 0.5 µg SauCas9 (GeneSnipper™ Cas9, BioVision) and 200 ng Phosphorothioate-modified guide sgRNAs against the Il1a (#51-53) and IL1b (#54-56) genes.

FIG. 1B illustrates agarose gel electrophoresis analysis of 100 ng mouse DNA, cleaved by 0.5 μg Sau Cas9 and 200 ng modified guide RNA's 51-53 for Il1a gene and 54-56 for Il1b. DNA is cut at a specific site by the Cas9 using the guide RNA to create a predictable band pattern on the agarose gel compared to the uncut control.

Editing Cell Lines

Genomic DNA was extracted from the edited pools and the Il1a or Il1b exon 4 was PCR amplified in the appropriate pools. The PCR products were sent for Sanger sequencing and then deconvoluted using TIDE or Synthego ICE software. Synthego ICE was used to deconvolute the Spy Cas9 pools. The software can determine the patterns of editing in each pool based on the guide RNA sequence and PAM site. It can distinguish between editing which has caused an in frame deletion that could lead to a truncated functional protein, and editing which has causes a frameshift mutation which will lead to a true knockout. The SauCas9 pools were analysed with TIDE because Synthego ICE software cannot deconvolute SauCas9 editing. TIDE analysis works in a similar way to ICE by determining patterns of editing in a pool based on the guide RNA and PAM site. However, rather than giving a true knockout score, it gives an editing efficiency score, which cannot distinguish between in frame and frameshift editing patterns. Therefore, editing efficiency scores may over represent the guide RNA's ability to knockout a protein. SpyCas9 is the standard protein used in CRISPR gene editing. However, it is 4101 bp compared to Sau Cas9 which is 3156 bp. Due to the size limitations of packaging some viruses, such as AAV, it was decided to compare the editing capabilities of SauCas9 and SpyCas9 to see whether the smaller Sau Cas9 could be used in the vector being designed for this project.

Figure 2A:
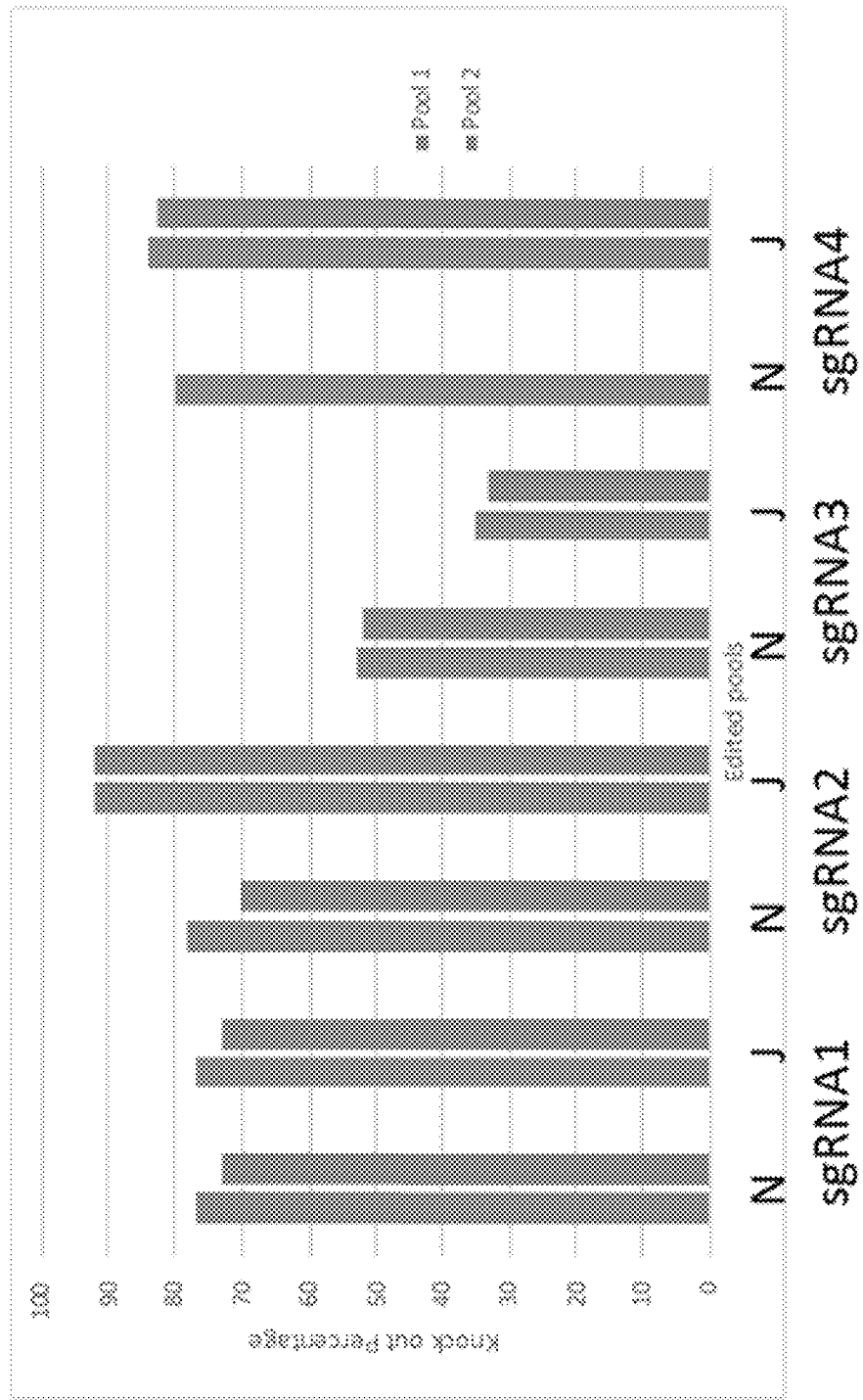
FIGS. 2A-2D illustrate graphs displaying editing efficiencies of SpyCas9 and SauCas9 used with a range of guide RNA's in J774.2 ("J") and NIH3T3 ("N") cells.
Figure 2B:
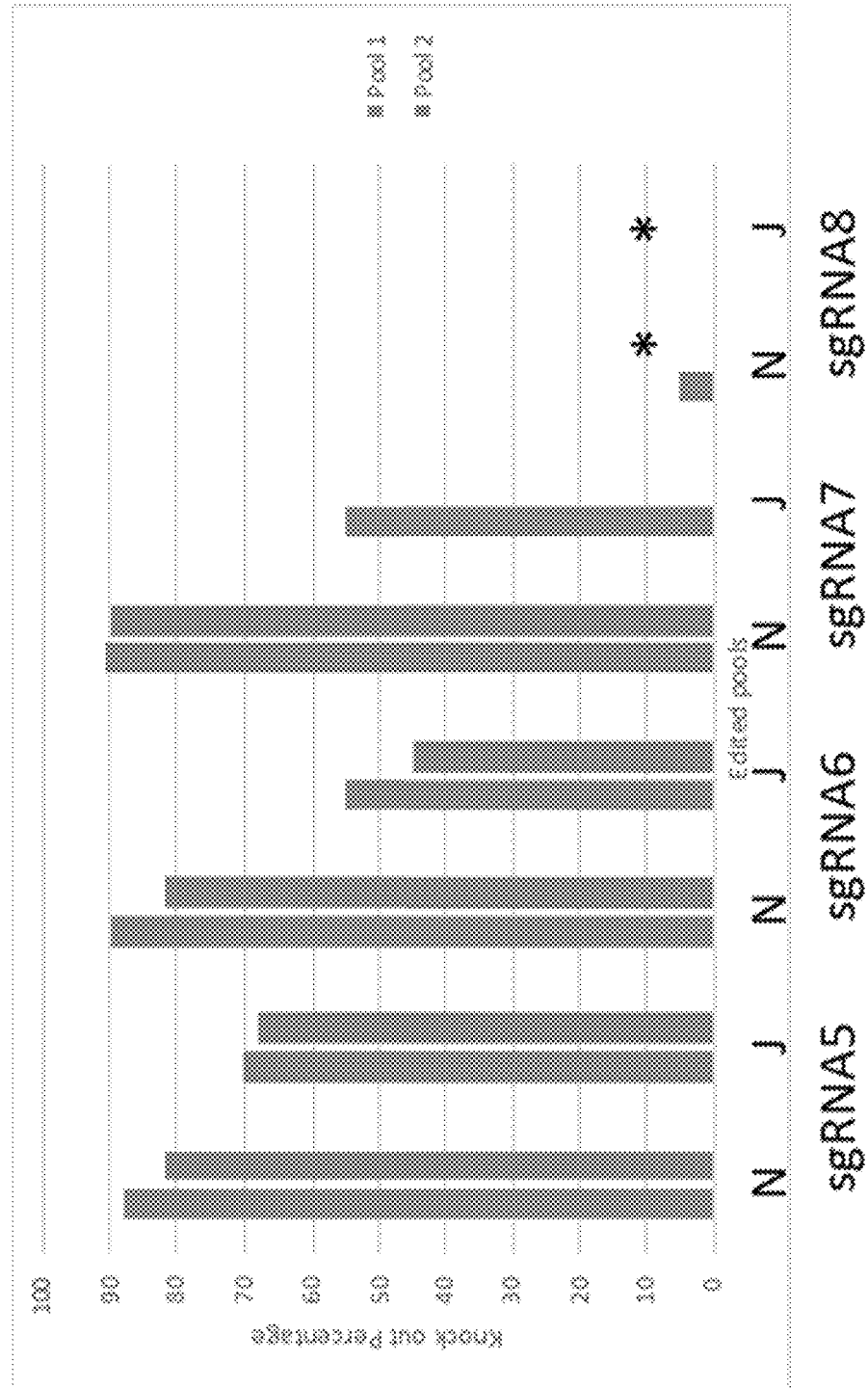
Figure 2C:
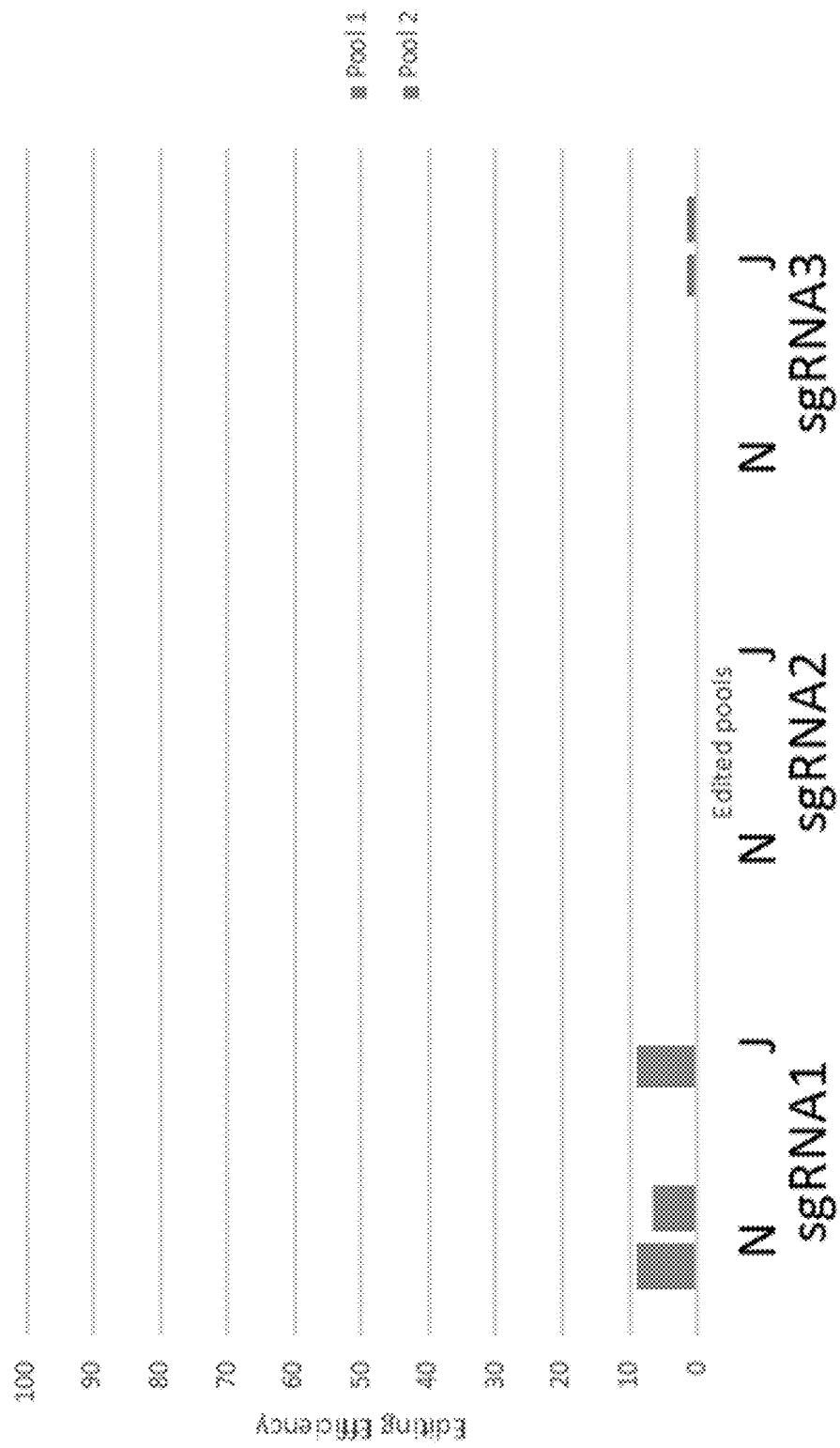
Figure 2D:
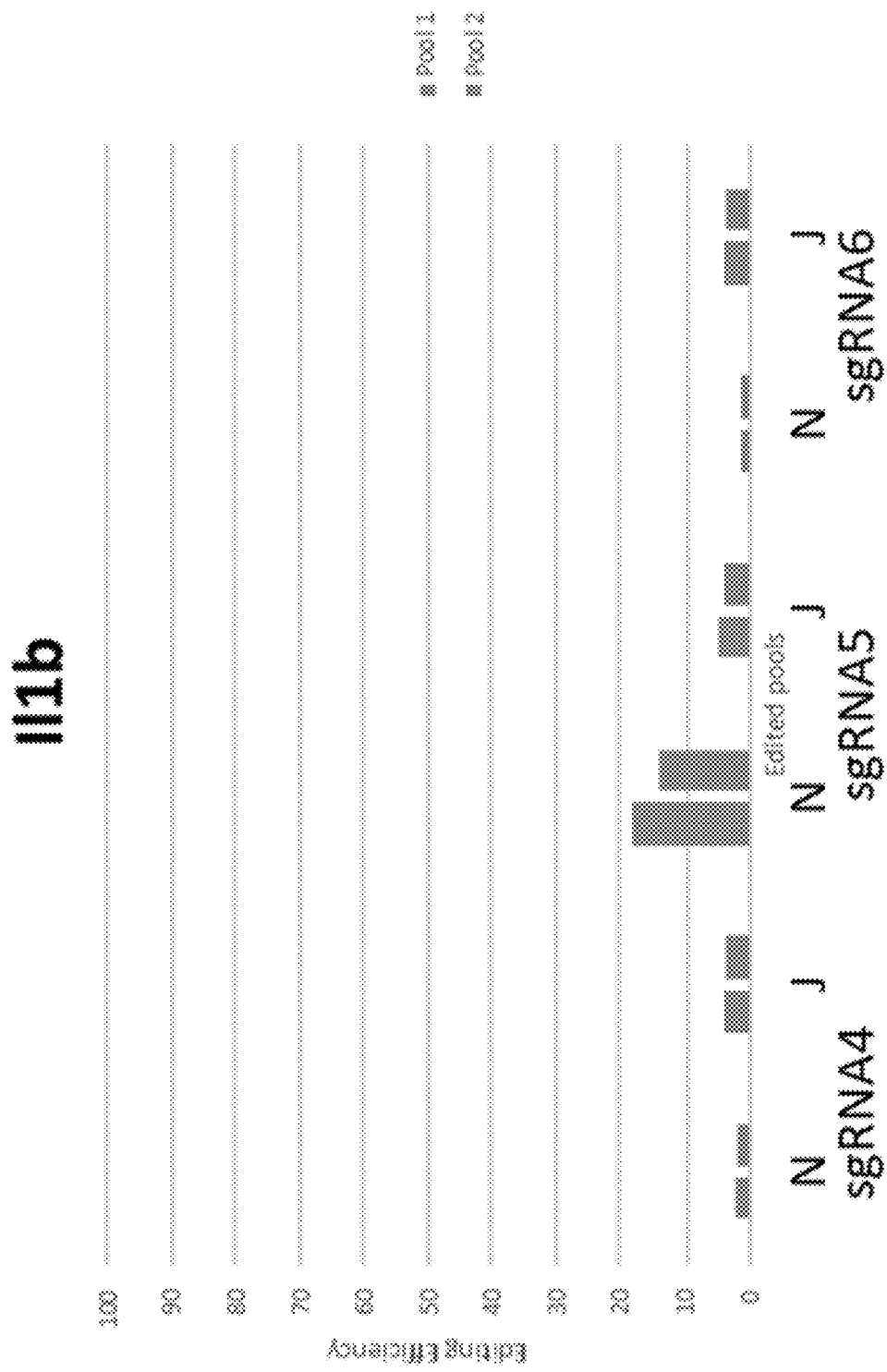

FIGS. 2A-2D illustrate graphs displaying editing efficiencies of Spy Cas9 (FIGS. 2A and 2B) and SauCas9 (FIGS. 2C and 2D) used with a range of guide RNA's in J774.2 ("J") and NIH3T3 ("N") cells. Editing efficiencies were determined using Synthego ICE or TIDE sanger deconvolution software. FIG. 2A: knock out efficiency of Il1a using guide RNA 43-46 with SpyCas9 in J774.2 and NIH3T3. Synthego ICE was used to deconvolute the sanger sequence trace and determine knock out efficiency. FIG. 2B: knock out efficiency of Il1b using guide RNA 47-50 with SpyCas9 in J774.2 and NIH3T3; without wishing to be bound by any particular theory, the data for sgRNA8 appears to show a failed synthesis. Synthego ICE was used to deconvolute the sanger sequence trace and determine knock out efficiency. FIG. 2C: knock out efficiency of Il1a using guide RNA 51-53 with saCas9 in J774.2 and NIH3T3. TIDE was used to deconvolute the sanger sequence trace and determine the editing efficiency. FIG. 2D: knock out efficiency of Il1b using guide RNA 54-56 with Sau Cas9 in J774.2 and NIH3T3. TIDE was used to deconvolute the sanger sequence trace and determine the editing efficiency.

Example 3. Reducing IL-1β Expression by CRISPR Gene-Engineering in a Mouse Uric Acid Model Time Course Experiment to Determine Optimal Pre-Treatment Time A pilot experiment is performed to determine optimal pre-treatment time of mice with virus prior to challenging the mice with uric acid. Mice are injected with GFP-labeled AAV5 vector into the knee joint. Viral load is then quantified by PCR and location of viral infection is quantified by histology at 3, 5, and 7 days after infection. A treatment time that yields robust expression of virus inside the joint is selected as the optimal lead time for injecting viral vectors into the mice for the experiments to determine the reduction of IL-1b in a mouse uric acid model by a CRISPR AAV vector engineered to target IL-1b and silence or reduce expression of IL-1b.

Experiment to Confirm CRISPR AAV (AAV-spCas9) Knock Down of IL-1b Expression and Treatment Effect in Uric Acid Model Mice are selected and distributed into three groups:
Group 1: mice injected with a CRISPR AAV vector (AAV-spCas9) engineered to target IL-1b, and silence or reduce expression of IL-1 protein,
Group 2: mice injected with "scrambled" guide RNA/Cas9 (AAV-spCas9), a CRISPR AAV vector engineered with a payload that will not affect IL-1 production, and
Group 3: mice injected with saline.

The mice are then challenged with uric acid after an optimal pre-treatment time. Within 24 hours of injection with uric acid, the animals are sacrificed and the joint tissue is analyzed for cytokine expression (e.g., assessed for IL-1 expression by IHC). The joint tissue may also be assessed for gross histopathology and for expression of biomarkers of inflammation.

Group 1 mice treated with a CRISPR AAV vector engineered to target IL-1b, and silence or reduce the expression of IL-1 protein, will show reduced levels of IL-1 by IHC and lower levels of inflammation biomarkers than any of the two other groups.

Example 4. Time Course Study of Intra-Articular Injection of AAV in Mice

A study was conducted to evaluate the time course for injecting AAV into the joint of male C57BL/6 mice.

Materials & Methods

Test Article Identification and Preparation—The eGFP AAVPrime™ Purified Adeno-associated Viral Particles: GFP-tagged AAV5 GeneCopoeia™, catalogue No. AB201, lot No. GC08222K1902, $1.18 \times 10^{13}$ Genome Copies/mL) and AAV6 (GeneCopoeia™, catalogue No. AB401, lot No. GC09242K1905, $5.47 \times 10^{12}$ Genome Copies/mL) we supplied. AAV-particles were shipped on dry ice and were stored at −80° C. immediately upon receipt. Just prior to dosing, the AAV-particles were reconstituted in phosphate buffered saline (PBS without calcium and magnesium: Corning, lot No. 11419005) for IA dosing at 10 μL per knee. See the study protocol (Appendix A) for additional details of test article preparation, storage, and handling.

Test System Identification—Male C57BL/6 mice (N=30) that were 8 to 10 weeks old were obtained from The Jackson Laboratory (Bar Harbor, Me.). The mice weighed approximately 24 to 29 grams (mean of 26 g) at enrollment on study day 0. The animals were identified by a distinct mark at the base of the tail delineating group and animal number. After randomization, all cages were labeled with protocol number, group numbers, and animal numbers with appropriate color-coding (Appendix A).

Environment & Husbandry—Upon arrival, the animals were housed 3 to 5 per cage in polycarbonate cages with wood chip bedding and suspended food and water bottles.

The mice were housed either in shoebox cages (static airflow, approximately 70 in2 floor space) with filter tops or in individually ventilated pie cages (passive airflow, approximately 70-75 in2 floor space). Animal care including room, cage, and equipment sanitation conformed to the guidelines cited in the Guide for the Care and Use of Laboratory Animals (Guide, 2011) and the applicable Bolder BioPATH SOPs.

The animals were acclimated for 4 days prior to being paced in the study. An attending veterinarian was on site or on call during the live phase of the study. No concurrent medications were given.

During the acclimation and study periods, the animals were housed in a laboratory environment with temperatures ranging 19° C. to 25° C. and relative humidity of 30% to 70%. Automatic timers provided 12 hours of light and 12 hours of dark. The animals were allowed access ad libitum to Envigo Teklad 8640 diet and fresh municipal tap water.

Experimental Design—On study day 0, the mice were randomized by body weight into treatment groups. Following randomization, the animals were dosed by intra-articular (IA) injection as indicated in Table 4. Animal body weights were measured as described in section 8.5.1. The mice were euthanized for necropsy and tissue collection at 3 time points (days 3, 5, and 7) as described below in the section titled 'Necropsy Specimens'.

TABLE 4

Group and Treatment Information

| Group | N | Treatment | Dose Level (particles) | Dose Vol. | Dose Conc. (particles/ml) | Dose Route | Regimen |
|---|---|---|---|---|---|---|---|
| 1 | 30 | GFP-tagged AAV5 | $5 \times 10^9$ | 10 μL | $5 \times 10^{11}$/mL | IA (right knee) | 1× (Day 0) |
|  |  | GFP-tagged AAV6 | $5 \times 10^9$ | 10 μL | $5 \times 10^{11}$/mL | IA (left knee) | 1× (Day 0) |

Observations, Measurements, and Specimens

Body Weight Measurements—The mice were weighed for randomization on study day 0 and again on days 1, 3, 5, and 7. Body weight measurements can be found in Table 6.

Necropsy Specimens—The mice were necropsied on study days 3, 5, and 7 as indicated in Table 5.

TABLE 5

Necropsy Schedule

| Group | Animal No. | Time-point(s) |
|---|---|---|
| 1 | 1-10 | Day 3 |
| 1 | 11-20 | Day 5 |
| 1 | 21-30 | Day 7 |

At necropsy, the mice were bled to exsanguination via cardiac puncture followed by cervical dislocation. Right and left knees were harvested from all animals. The skin and muscle were removed from the joints while keeping the joint capsule intact. Joints were flash-frozen separately in 15-mL conical tubes labeled with only mouse number, day of collection, and right or left leg. Knee joints were stored frozen at −80° C. for shipment.

Animal Disposition—Animal carcasses were disposed of according to BBP SOPS.

Specimen and Raw Data Storage—Specimens (right and left knee joints), study data, and reports were delivered during or at the completion of the study.

Statement of Effect of Deviations on the Quality and Integrity of the Study—There were no deviations from the study protocol.

Results/Conclusions

On study day 0, male C57BL/6 mice received IA injections of GFP-tagged AAV5 ($5 \times 10^9$ particles, 10 μL) into right knees and IA injections of GFP-tagged AAV6 ($5 \times 10^9$ particles, 10 μL) into left knees. The animals were weighed on study days 0, 1, 3, 5, and 7. Necropsies were performed on study day 3 (animals 1-10), day 5 (animals 11-20), and day 7 (animals 21-30), and right and left knee joints were collected for shipment. The live portion of this study was completed successfully including animal weighing, dosing, and biological sample collection. All animals survived to study termination.

REFERENCES

Guide for the Care and Use of Laboratory Animals (8th Edition). National Research Council, National Academy of Sciences, Washington, D C, 2011, which is incorporated by reference herein in its entirety for all purposes.

TABLE 6

Body Weight and Dose Calculation Data (MTC-UCM-1)

| Treatment Group | Day 0 | Day 0 | Day 1 | | Day 3 | |
|---|---|---|---|---|---|---|
| Group 1- C57Bl/6 IA, 1× (D0) | Body Wt. (g) | Dose Vol. 10 μl (ml) | Body Wt. (g) | Body Wt. % Δ Baseline | Body Wt. (g) | Body Wt. Baseline |
| 1 | 26.68 | 0.01 | 26.53 | −0.6% | 26.22 | −1.7% |
| 2 | 27.65 | 0.01 | 27.55 | −0.4% | 26.54 | −4.0% |
| 3 | 28.64 | 0.01 | 27.97 | −2.3% | 28.57 | −0.2% |
| 4 | 28.13 | 0.01 | 27.60 | −1.9% | 27.63 | −1.8% |
| 5 | 26.18 | 0.01 | 26.07 | −0.4% | 25.87 | −1.2% |
| 6 | 26.38 | 0.01 | 26.02 | −1.4% | 26.30 | −0.3% |
| 7 | 29.13 | 0.01 | 29.11 | −0.1% | 28.83 | 1.0% |
| 8 | 24.22 | 0.01 | 23.90 | −1.3% | 23.51 | −2.9% |
| 9 | 25.40 | 0.01 | 24.97 | −1.7% | 24.49 | −3.6% |
| 10 | 24.85 | 0.01 | 24.21 | −2.6% | 23.86 | −4.0% |
| 11 | 27.76 | 0.01 | 27.26 | −1.8% | 28.02 | 0.9% |
| 12 | 25.23 | 0.01 | 24.77 | 1.8% | 24.90 | 1.3% |
| 13 | 24.92 | 0.01 | 24.45 | −1.9% | 24.59 | −1.3% |
| 14 | 24.33 | 0.01 | 24.19 | −0.6% | 23.86 | −1.9% |
| 15 | 23.82 | 0.01 | 23.81 | 0.0% | 23.26 | −2.4% |
| 16 | 24.83 | 0.01 | 24.39 | −1.8% | 24.15 | −2.7% |
| 17 | 25.94 | 0.01 | 25.93 | 0.0% | 26.28 | 1.3% |
| 18 | 27.21 | 0.01 | 27.44 | 0.8% | 27.60 | 1.4% |
| 19 | 25.61 | 0.01 | 25.17 | −1.7% | 25.22 | −1.5% |
| 20 | 27.81 | 0.01 | 27.26 | −2.0% | 26.99 | −2.9% |
| 21 | 26.63 | 0.01 | 26.63 | 0.0% | 26.71 | 0.3% |
| 22 | 26.96 | 0.01 | 27.40 | 1.6% | 25.75 | −4.5% |
| 23 | 27.69 | 0.01 | 27.21 | −1.7% | 27.22 | −1.7% |
| 24 | 25.90 | 0.01 | 25.71 | −0.7% | 25.45 | −1.7% |
| 25 | 24.03 | 0.01 | 24.11 | 0.3% | 23.40 | −2.6% |
| 26 | 27.60 | 0.01 | 26.67 | −3.4% | 27.00 | −2.2% |
| 27 | 27.87 | 0.01 | 27.59 | −1.0% | 27.22 | −2.3% |
| 28 | 24.43 | 0.01 | 24.25 | −0.7% | 24.14 | 1.2% |
| 29 | 26.75 | 0.01 | 26.02 | −2.7% | 26.46 | −1.1% |
| 30 | 25.93 | 0.01 | 25.99 | 0.2% | 25.80 | −0.5% |
| Mean | 26.28 |  | 26.01 | −1.0% | 25.86 | −1.6% |
| SE | 0.27 |  | 0.27 | 0.2% | 0.29 | 0.3% |

TABLE 6-continued

Body Weight and Dose Calculation Data (MTC-UCM-1)

| Treatment Group | Day 5 | | Day 7 | | |
| --- | --- | --- | --- | --- | --- |
| Group 1-C57Bl/6 IA, 1× (D0) | Body Wt. (g) | Body Wt. % Δ Baseline | Body Wt. (g) | Body Wt. % Δ Baseline | Change in Body weight from Baseline (g) |
| 1 | | | | | −0.46 |
| 2 | | | | | −1.11 |
| 3 | | | | | −0.07 |
| 4 | | | | | −0.50 |
| 5 | | | | | −0.31 |
| 6 | | | | | 0.08 |
| 7 | | | | | −0.30 |
| 8 | | | | | −0.71 |
| 9 | | | | | −0.91 |
| 10 | | | | | −0.99 |
| 11 | 28.62 | 3.1% | | | 0.86 |
| 12 | 25.04 | −0.8% | | | −0.19 |
| 13 | 24.94 | 0.1% | | | 0.02 |
| 14 | 23.68 | −2.7% | | | −0.65 |
| 15 | 23.71 | −0.5% | | | −0.11 |
| 16 | 24.26 | −2.3% | | | −0.57 |
| 17 | 26.15 | 0.8% | | | 0.21 |
| 18 | 27.88 | 2.5% | | | 0.67 |
| 19 | 25.64 | 0.1% | | | 0.03 |
| 20 | 27.71 | −0.4% | | | −0.10 |
| 21 | 26.44 | −0.7% | 26.70 | 0.3% | 0.07 |
| 22 | 25.76 | −4.5% | 25.75 | −4.5% | −1.21 |
| 23 | 27.53 | −0.6% | 27.33 | −1.3% | −0.36 |
| 24 | 25.61 | −1.1% | 26.00 | 0.4% | 0.10 |
| 25 | 23.76 | −1.1% | 24.10 | 0.3% | 0.07 |
| 26 | 27.44 | −0.6% | 27.18 | −1.5% | −0.42 |
| 27 | 27.09 | −2.8% | 27.30 | −2.0% | −0.57 |
| 28 | 24.50 | 0.3% | 24.76 | 1.4% | 0.33 |
| 29 | 26.48 | −1.0% | 26.48 | −1.0% | −0.27 |
| 30 | 25.73 | −0.8% | 25.89 | 0.2% | −0.04 |
| Mean | 25.90 | −0.6% | 26.15 | −0.8% | −0.25 |
| SE | 0.33 | 0.4% | 0.34 | 0.5% | 0.09 |

Protocol

Test System

Number of animals: 33 (30+3 extra)

Species/Strain or Breed: C57BL/6

Vendor: Jackson

Age/Wt at Arrival: 8-10 weeks old (~20 grams)

Gender: Male

Age/Wt Range at Study Initiation: At least 9 weeks by study initiation

Acclimation: Will be acclimated for at least 3 days after arrival at BBP

Housing: 3-5 animals/cage

Study Calendar

| Mon | Tue | Wed | Thu | Fri | Sat | Sun |
| --- | --- | --- | --- | --- | --- | --- |
| Week 1 Day -4 | Week 1 Day -3 | Week 1 Day -2 | Week 1 Day -1 | Week 1 Day 0 | Week 1 Day 1 | Week 1 Day 2 |
| Distribute animals on arrival into groups for acclimation | | | | Weigh & Randomize. IA Injections | Weigh | |
| Mon | Tue | Wed | Thu | Fri | Sat | Sun |
| Week 2 Day 3 | Week 2 Day 4 | Week 2 Day 5 | Week 2 Day 6 | Week 2 Day 7 | Week 2 Day 8 | Week 2 Day 9 |
| Weigh, Necropsy Animals 1-10 | | Weigh, Necropsy Animals 11-20 | | Weigh, Necropsy Animals 21-30 | | |

Materials

| Name | Supplier | Cat #* |
| --- | --- | --- |
| Isoflurane | VetOne | 502017 |
| Syringes & Needles | BD | As needed |
| Serum Separator Tubes (if needed) | Greiner Bio-One | #450472 (via Fisher) |
| Li Hep Mini-Collect (if needed) | Greiner Bio-One | #450480 (via Fisher) |
| EDTA Mini-Collect (if needed) | Greiner Bio-One | #450477 (via Fisher) |
| K3EDTA (if needed) | Covidien | #8881311149 (via Fisher) |
| K2EDTA Vacutainer (if needed) | BD | #367856 (via Fisher) |
| Na Hep Vacutainer (if needed) | BD | #367871 (via Fisher) |
| Li Hep Vacutainer (if needed) | BD | #367960 (via Fisher) |

Test Article and Vehicle Information

Unformulated Test Article Storage Conditions—GFP-tagged AAV5 (Group 1): −80 C; GFP-tagged AAV6 (Group 1):—80° C.

Vehicle Information—GFP-tagged AAV5 (Group 1): PBS (w/o Ca & Mg); GFP-tagged AAV6 (Group 1): PBS (w/o Ca & Mg).

Test Article Formulation Instructions & Calculations—GFP-tagged AAV5 (Group 1): Dilute stock to appropriate concentration using PBS; GFP-tagged AAV6 (Group 1): Dilute stock to appropriate concentration using PBS.

Dosing Formulations and Vehicle Storage & Stability—GFP-tagged AAV5 (Group 1): Dilute just prior to injecting; GFP-tagged AAV6 (Group 1): Dilute just prior to injecting.

Disposition of Test Articles Following Dosing—GFP-tagged AAV5 (Group 1): Discard formulations, retain stock solution for future studies; GFP-tagged AAV6 (Group 1): Discard formulations, retain stock solution for future studies.

Live Phase Deliverables

| Live Phase Data Collection | | | |
| --- | --- | --- | --- |
| Type | Study Day | Grp (An) | Details |
| Body Weight | Day 0, 1, 3, 5, 7 | All (Remaining) | |

Necropsy Information
  Sacrifice Schedule: Group 1 An 1-10: Day 3
    Group 1 An 11-20: Day 5
    Group 1 An 21-30: Day 7
  Method of Euthanasia: Bleed by cardiac puncture to exsanguinate followed by cervical dislocation.
  Time Points: Not Timed Necropsy Tissue Sample Collection:

| Type | Gr/An | Details | Storage Condition | Disposition |
|---|---|---|---|---|
| Right Injected Knee | All | Remove skin and muscle keeping joint capsule intact | Flash Freeze (15 ml conical vial*) | Ship |
| Left Injected Knee | All | Remove skin and muscle keeping joint capsule intact | Flash Freeze (15 ml conical vial*) | Ship |

Sample Analysis

Tissue Specimens—Hind limbs from AAV-injected mice were snap-frozen and shipped. On arrival, specimens were transferred to the −80° C. freezer for storage.

GFP Expression in Target Tissues—Hind limbs (paired) were thawed at room temperature and imaged in an IVIS bioluminescence imaging system (Lumina III; Perkin Elmer). GFP fluorescence was quantified using excitation at 488 nm and measuring emission at 510 nm. A total of 4 mice were evaluated at each time point (3 days, 5 days and 7 days). Tissues from the remaining 6 animals at each time point were retained for subsequent confirmation of viral burden using real-time PCR.

Figure 3:
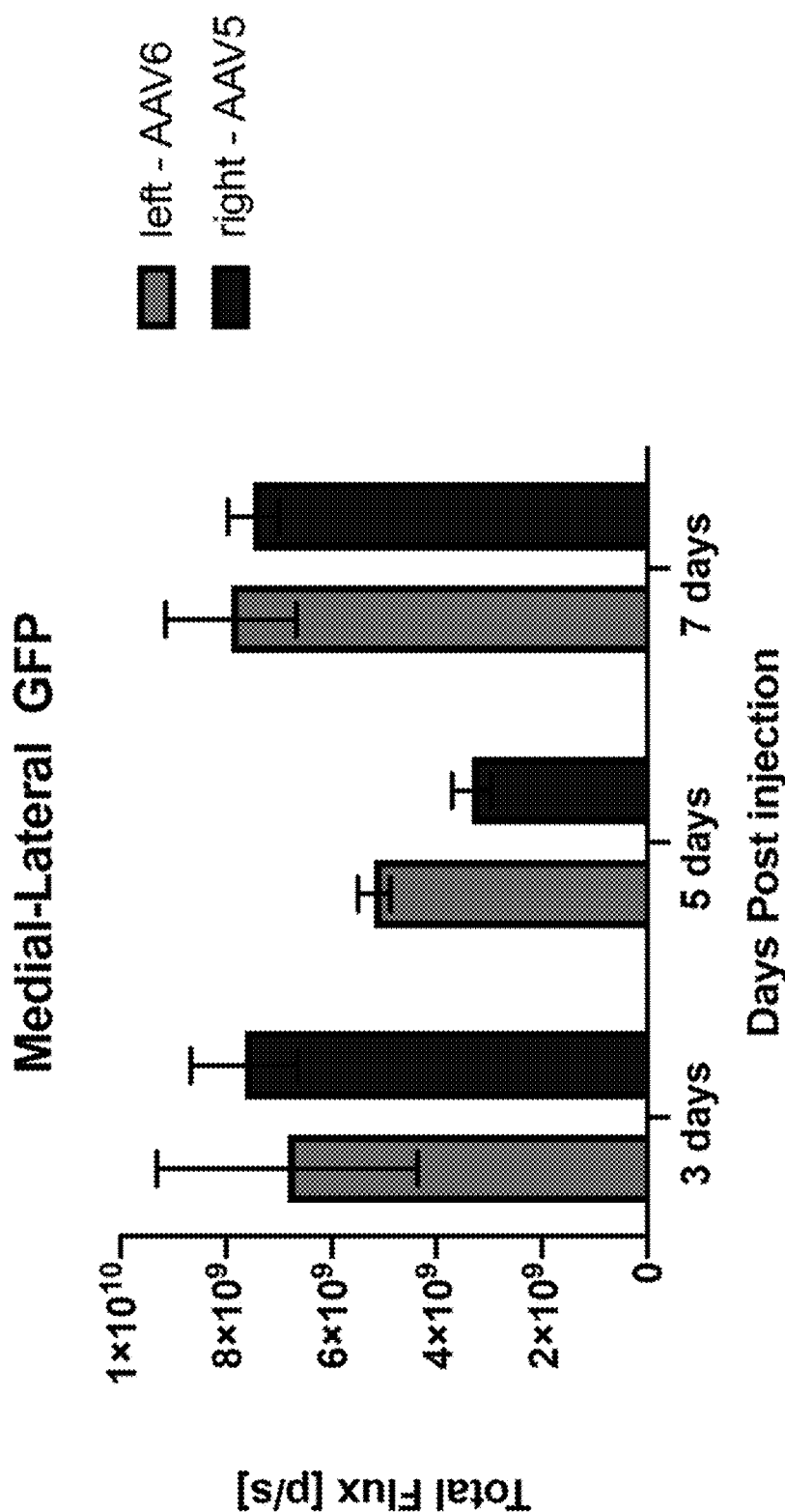
FIG. 3 illustrates GFP expression measured using the IVIS system. Flux values were based on a region of interest centred on the animal's injected knee joint. Data are presented as mean (SD) for four specimens per group.

Results—As can be seen in FIG. 3, there was high-level expression of GFP within injected knee joints at 3 days post-injection. Viral loads decreased slightly at 5 days, then rose again to 7 days. With the limited sample size in this pilot study there was no significant difference between the behaviours of AAV-5 and AAV-6.

Discussion—The data from this study support the use of either AAV-5 or AAV-6 for intra-articular delivery of CRISPR-Cas9 into the mouse knee joint. The levels of both viral serotypes increased from 5 to 7 day, leaving open the possibility that they may have increased further if the follow-up had been extended to 2 or maybe 3 weeks. Additional work would be needed to confirm this, but the data thus far would suggest that there should be an interval of at least one week before the injection of the vector and challenge with intra-articular monoiodoacetate (MIA) crystals.

Background & Rationale—The monoiodoacetate (MIA)-induced OA model is used in this work for two reasons. First, natural (spontaneous) OA is extremely uncommon in mice, whereas the injection of MIA results in an induced model of OA that is relatively fast in onset, predictable and that provides good clinical correlation to the disease phenotype see in human OA patients, including intra-articular inflammation, pain and cartilage degeneration. Second, in contrast with surgical models such as destabilization of the medial meniscus (DMM) and transection of the anterior cruciate ligament (ACLT), the MIA model does not involve surgical incision of the joint capsule, making it much more relevant to the capsules of human patients with OA.

Injection of MIA crystals in rodents reproduces OA-like lesions and functional impairment that can be analyzed and quantified by techniques such as behavioral testing and objective lameness assessment. MIA is an inhibitor of glyceraldehyde-3-phosphatase and the resulting alterations in cellular glycolysis eventual cause the death of cells within the joint, including chondrocytes. Chondrocyte death manifests as cartilage degeneration and alterations in proteoglycan staining. Mice injected with MIA usually exhibit pain-like behavior within 72 hours, and cartilage loss by around 4 weeks post-injection. Increases in IL-1 expression have been documented within 2-3 days of injection in rats and in mice.

Study Design—Mice are injected unilaterally with either MIA or the saline vehicle control (one joint per animal). Within each group, half of the animals are pre-treated with the AAV-CRISPR-Cas9 vector targeting the mouse IL-1 beta gene, and the other half are injected with an AAV-CRISPR-Cas9 scrambled control. Animals from both groups will be taken off study at one of two time points: an early time point of 48 hours, to allow for assessment of the impact of therapy on the levels of IL-1 within the synovial fluid, and a late time point of 4 weeks to allow for assessment of the impact of therapy on cartilage breakdown and histological evidence of osteoarthritis.

Methods

Experimental Animals—A total of 80 mice are used in this study.

The experimental procedures are reviewed and approved by the local IACUC. Mice are housed in micro-isolator cages, fed a standard laboratory animal diet, and allowed access to water ad libitum.

MIA Model & Anti-IL1 Therapy—Mice are acclimated for a period of 7 days ahead of the study. On the first day of the study, mice are anaesthetized with an inhaled mixture of isoflurane in oxygen. Once a surgical plane of anesthesia has been confirmed, the right hind limb is clipped and the skin scrubbed with a surgical antiseptic. 40 mice (Treated) receive an intra-articular injection of the AAV-CRISPR-Cas9 vector targeting IL-1, and the remaining 40 animals (Control) are injected intra-articularly with the AAV-CRISPR-Cas9 scrambled control. Seven days later, half of the animals in each group are injected in the same joint with MIA and half with the saline vehicle. This leads to the establishment of four study groups:
  Group 1: Treated-MIA (20 mice)
  Group 2: Control-MIA (20 mice)
  Group 3: Treated-Vehicle (20 mice)
  Group 4: Control-Vehicle (20 mice)

Ten mice per group are euthanised 48 hours after the MIA challenge in order to document IL-1 levels in the knee joint. The remaining animals will be housed for 4 weeks in order to evaluate the effects of therapy on pain behavior (behavioral testing, including von Frey testing), lameness (limb use), joint swelling (caliper measurement) and joint pathology (histopathology).

Euthanasia & Tissue Collection—Mice are killed by exsanguination, followed by cervical dislocation. Joints are opened and either flushed for IL-1 measurement (48-hour group) or immersion fixed in 10% formalin for decalcified histopathology (4-week group).

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

It is to be understood that the methods described herein are not limited to the particular methodology, protocols, subjects, and sequencing techniques described herein and as such can vary. It is also to be understood that the terminology used herein is for the purpose of describing particular embodiments only, and is not intended to limit the scope of the methods and compositions described herein, which will be limited only by the appended claims. While some embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

Several aspects are described with reference to example applications for illustration. Unless otherwise indicated, any embodiment can be combined with any other embodiment. It should be understood that numerous specific details, relationships, and methods are set forth to provide a full understanding of the features described herein. A skilled artisan, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

While some embodiments have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention.

Furthermore, it shall be understood that all aspects of the invention are not limited to the specific depictions, configurations or relative proportions set forth herein which depend upon a variety of conditions and variables. It should be understood that various alternatives to the embodiments of the invention described herein can be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

---

The invention claimed is:

1. A pharmaceutical composition for the treatment or prevention of a joint disease or condition, comprising:
   a therapeutically effective amount of a Clustered Regularly Interspaced Short Palindromic Repeats (CRISPR) gene-editing system, the system comprising:
   (i) a nucleic acid encoding a CRISPR Associated Protein 9 (Cas9) protein; and
   (ii) at least one guide RNA targeting an IL-1α gene, wherein:
      the at least one guide RNA comprises a crRNA sequence that is complementary to a target sequence in exon 4 of the IL-1α gene, and
      the target sequence is adjacent to a protospacer adjacent motif (PAM) sequence for the Cas9 protein.

2. The pharmaceutical composition of claim 1, wherein the composition comprises one or more liposomes collectively comprising the CRISPR gene-editing system.

3. The pharmaceutical composition of claim 1, wherein the CRISPR gene-editing system are present in a naked state.

4. The pharmaceutical composition of claim 1, wherein the Cas9 protein is an S. pyogenes Cas9 polypeptide.

5. The pharmaceutical composition of claim 1, wherein the Cas9 protein is an S. aureus Cas9 polypeptide.

6. The pharmaceutical composition of claim 1, wherein the IL-1α gene is a human IL-1α gene.

7. The pharmaceutical composition of claim 1, wherein the IL-1α gene is a canine IL-1α gene.

8. The pharmaceutical composition of claim 1, wherein the IL-1α gene is an equine IL-1α gene.

9. The pharmaceutical composition of claim 1, wherein the composition is formulated for parenteral administration.

10. The pharmaceutical composition of claim 1, wherein the composition is formulated for intra-articular injection within a joint of a subject.

11. A pharmaceutical composition for the treatment or prevention of a joint disease or condition, comprising:
   a therapeutically effective amount of a Clustered Regularly Interspaced Short Palindromic Repeats (CRISPR) gene-editing system, the system comprising:
   (i) a nucleic acid encoding a CRISPR Associated Protein 9 (Cas9) protein; and
   (ii) at least one guide RNA targeting an IL-1β gene, wherein:
      the at least one guide RNA comprises a crRNA sequence that is complementary to a target sequence in exon 4 of the IL-1β gene, and
      the target sequence is adjacent to a protospacer adjacent motif (PAM) sequence for the Cas9 protein.

12. The pharmaceutical composition of claim 11, wherein the composition comprises one or more liposomes collectively comprising the CRISPR gene-editing system.

13. The pharmaceutical composition of claim 11, wherein the CRISPR gene-editing system are present in a naked state.

14. The pharmaceutical composition of claim 11, wherein the Cas9 protein is an S. pyogenes Cas9 polypeptide.

15. The pharmaceutical composition of claim 11, wherein the Cas9 protein is an *S. aureus* Cas9 polypeptide.

16. The pharmaceutical composition of claim 11, wherein the IL-1β gene is a human IL-1β gene.

17. The pharmaceutical composition of claim 11, wherein the IL-1β gene is a canine IL-1β gene.

18. The pharmaceutical composition of claim 11, wherein the IL-1β gene is an equine IL-1β gene.

19. The pharmaceutical composition of claim 11, wherein the composition is formulated for parenteral administration.

20. The pharmaceutical composition of claim 11, wherein the composition is formulated for intra-articular injection within a joint of a subject.

* * * * *

SEQUENCE LISTING

```
<160> NUMBER OF SEQ ID NOS: 36

<210> SEQ ID NO 1
<211> LENGTH: 271
<212> TYPE: PRT
<213> ORGANISM: Homo sapiens

<400> SEQUENCE: 1

Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
            20                  25                  30

Lys Ser Phe Tyr His Val Ser Tyr Gly Pro Leu His Glu Gly Cys Met
        35                  40                  45

Asp Gln Ser Val Ser Leu Ser Ile Ser Glu Thr Ser Lys Thr Ser Lys
    50                  55                  60

Leu Thr Phe Lys Glu Ser Met Val Val Val Ala Thr Asn Gly Lys Val
65                  70                  75                  80

Leu Lys Lys Arg Arg Leu Ser Leu Ser Gln Ser Ile Thr Asp Asp Asp
                85                  90                  95

Leu Glu Ala Ile Ala Asn Asp Ser Glu Glu Glu Ile Ile Lys Pro Arg
            100                 105                 110

Ser Ala Pro Phe Ser Phe Leu Ser Asn Val Lys Tyr Asn Phe Met Arg
        115                 120                 125
```

```
Ile Ile Lys Tyr Glu Phe Ile Leu Asn Asp Ala Leu Asn Gln Ser Ile
            130                 135                 140

Ile Arg Ala Asn Asp Gln Tyr Leu Thr Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
            180                 185                 190

Val Thr Ala Gln Asp Glu Asp Gln Pro Val Leu Leu Lys Glu Met Pro
        195                 200                 205

Glu Ile Pro Lys Thr Ile Thr Gly Ser Glu Thr Asn Leu Leu Phe Phe
210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                245                 250                 255

Gly Pro Pro Ser Ile Thr Asp Phe Gln Ile Leu Glu Asn Gln Ala
            260                 265                 270

<210> SEQ ID NO 2
<211> LENGTH: 269
<212> TYPE: PRT
<213> ORGANISM: Homo sapiens

<400> SEQUENCE: 2

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
210                 215                 220

Lys Leu Glu Phe Glu Ser Ala Gln Phe Pro Asn Trp Tyr Ile Ser Thr
```

```
              225                 230                 235                 240
Ser Gln Ala Glu Asn Met Pro Val Phe Leu Gly Gly Thr Lys Gly Gly
                    245                 250                 255

Gln Asp Ile Thr Asp Phe Thr Met Gln Phe Val Ser Ser
                260                 265
```

<210> SEQ ID NO 3
<211> LENGTH: 270
<212> TYPE: PRT
<213> ORGANISM: Mus musculus

<400> SEQUENCE: 3

```
Met Ala Lys Val Pro Asp Leu Phe Glu Asp Leu Lys Asn Cys Tyr Ser
1               5                   10                  15

Glu Asn Glu Asp Tyr Ser Ser Ala Ile Asp His Leu Ser Leu Asn Gln
                20                  25                  30

Lys Ser Phe Tyr Asp Ala Ser Tyr Gly Ser Leu His Glu Thr Cys Thr
            35                  40                  45

Asp Gln Phe Val Ser Leu Arg Thr Ser Glu Thr Ser Lys Met Ser Asn
        50                  55                  60

Phe Thr Phe Lys Glu Ser Arg Val Thr Val Ser Ala Thr Ser Ser Asn
65                  70                  75                  80

Gly Lys Ile Leu Lys Lys Arg Arg Leu Ser Phe Ser Glu Thr Phe Thr
                85                  90                  95

Glu Asp Asp Leu Gln Ser Ile Thr His Asp Leu Glu Glu Thr Ile Gln
                100                 105                 110

Pro Arg Ser Ala Pro Tyr Thr Tyr Gln Ser Asp Leu Arg Tyr Lys Leu
            115                 120                 125

Met Lys Leu Val Arg Gln Lys Phe Val Met Asn Asp Ser Leu Asn Gln
        130                 135                 140

Thr Ile Tyr Gln Asp Val Asp Lys His Tyr Leu Ser Thr Thr Trp Leu
145                 150                 155                 160

Asn Asp Leu Gln Gln Glu Val Lys Phe Asp Met Tyr Ala Tyr Ser Ser
                165                 170                 175

Gly Gly Asp Asp Ser Lys Tyr Pro Val Thr Leu Lys Ile Ser Asp Ser
            180                 185                 190

Gln Leu Phe Val Ser Ala Gln Gly Glu Asp Gln Pro Val Leu Leu Lys
        195                 200                 205

Glu Leu Pro Glu Thr Pro Lys Leu Ile Thr Gly Ser Glu Thr Asp Leu
    210                 215                 220

Ile Phe Phe Trp Lys Ser Ile Asn Ser Lys Asn Tyr Phe Thr Ser Ala
225                 230                 235                 240

Ala Tyr Pro Glu Leu Phe Ile Ala Thr Lys Glu Gln Ser Arg Val His
                245                 250                 255

Leu Ala Arg Gly Leu Pro Ser Met Thr Asp Phe Gln Ile Ser
            260                 265                 270
```

<210> SEQ ID NO 4
<211> LENGTH: 269
<212> TYPE: PRT
<213> ORGANISM: Mus musculus

<400> SEQUENCE: 4

```
Met Ala Thr Val Pro Glu Leu Asn Cys Glu Met Pro Pro Phe Asp Ser
1               5                   10                  15

Asp Glu Asn Asp Leu Phe Phe Glu Val Asp Gly Pro Gln Lys Met Lys
```

```
            20                  25                  30
Gly Cys Phe Gln Thr Phe Asp Leu Gly Cys Pro Asp Glu Ser Ile Gln
            35                  40                  45
Leu Gln Ile Ser Gln Gln His Ile Asn Lys Ser Phe Arg Gln Ala Val
    50                  55                  60
Ser Leu Ile Val Ala Val Glu Lys Leu Trp Gln Leu Pro Val Ser Phe
65                  70                  75                  80
Pro Trp Thr Phe Gln Asp Glu Asp Met Ser Thr Phe Phe Ser Phe Ile
                85                  90                  95
Phe Glu Glu Glu Pro Ile Leu Cys Asp Ser Trp Asp Asp Asp Asp Asn
            100                 105                 110
Leu Leu Val Cys Asp Val Pro Ile Arg Gln Leu His Tyr Arg Leu Arg
            115                 120                 125
Asp Glu Gln Gln Lys Ser Leu Val Leu Ser Asp Pro Tyr Glu Leu Lys
            130                 135                 140
Ala Leu His Leu Asn Gly Gln Asn Ile Asn Gln Gln Val Ile Phe Ser
145                 150                 155                 160
Met Ser Phe Val Gln Gly Glu Pro Ser Asn Asp Lys Ile Pro Val Ala
                165                 170                 175
Leu Gly Leu Lys Gly Lys Asn Leu Tyr Leu Ser Cys Val Met Lys Asp
            180                 185                 190
Gly Thr Pro Thr Leu Gln Leu Glu Ser Val Asp Pro Lys Gln Tyr Pro
            195                 200                 205
Lys Lys Lys Met Glu Lys Arg Phe Val Phe Asn Lys Ile Glu Val Lys
            210                 215                 220
Ser Lys Val Glu Phe Glu Ser Ala Glu Phe Pro Asn Trp Tyr Ile Ser
225                 230                 235                 240
Thr Ser Gln Ala Glu His Lys Pro Val Phe Leu Gly Asn Asn Ser Gly
                245                 250                 255
Gln Asp Ile Ile Asp Phe Thr Met Glu Ser Val Ser Ser
            260                 265

<210> SEQ ID NO 5
<211> LENGTH: 177
<212> TYPE: PRT
<213> ORGANISM: Homo sapiens

<400> SEQUENCE: 5

Met Glu Ile Cys Arg Gly Leu Arg Ser His Leu Ile Thr Leu Leu Leu
1               5                   10                  15
Phe Leu Phe His Ser Glu Thr Ile Cys Arg Pro Ser Gly Arg Lys Ser
                20                  25                  30
Ser Lys Met Gln Ala Phe Arg Ile Trp Asp Val Asn Gln Lys Thr Phe
            35                  40                  45
Tyr Leu Arg Asn Asn Gln Leu Val Ala Gly Tyr Leu Gln Gly Pro Asn
    50                  55                  60
Val Asn Leu Glu Glu Lys Ile Asp Val Val Pro Ile Glu Pro His Ala
65                  70                  75                  80
Leu Phe Leu Gly Ile His Gly Gly Lys Met Cys Leu Ser Cys Val Lys
                85                  90                  95
Ser Gly Asp Glu Thr Arg Leu Gln Leu Glu Ala Val Asn Ile Thr Asp
            100                 105                 110
Leu Ser Glu Asn Arg Lys Gln Asp Lys Arg Phe Ala Phe Ile Arg Ser
            115                 120                 125
```

```
Asp Ser Gly Pro Thr Thr Ser Phe Glu Ser Ala Ala Cys Pro Gly Trp
    130                 135                 140
Phe Leu Cys Thr Ala Met Glu Ala Asp Gln Pro Val Ser Leu Thr Asn
145                 150                 155                 160
Met Pro Asp Glu Gly Val Met Val Thr Lys Phe Tyr Phe Gln Glu Asp
                165                 170                 175
Glu
```

<210> SEQ ID NO 6
<211> LENGTH: 178
<212> TYPE: PRT
<213> ORGANISM: Mus musculus

<400> SEQUENCE: 6

```
Met Glu Ile Cys Trp Gly Pro Tyr Ser His Leu Ile Ser Leu Leu Leu
1               5                   10                  15
Ile Leu Leu Phe His Ser Glu Ala Ala Cys Arg Pro Ser Gly Lys Arg
                20                  25                  30
Pro Cys Lys Met Gln Ala Phe Arg Ile Trp Asp Thr Asn Gln Lys Thr
            35                  40                  45
Phe Tyr Leu Arg Asn Asn Gln Leu Ile Ala Gly Tyr Leu Gln Gly Pro
        50                  55                  60
Asn Ile Lys Leu Glu Glu Lys Ile Asp Met Val Pro Ile Asp Leu His
65                  70                  75                  80
Ser Val Phe Leu Gly Ile His Gly Gly Lys Leu Cys Leu Ser Cys Ala
                85                  90                  95
Lys Ser Gly Asp Asp Ile Lys Leu Gln Leu Glu Glu Val Asn Ile Thr
            100                 105                 110
Asp Leu Ser Lys Asn Lys Glu Glu Asp Lys Arg Phe Thr Phe Ile Arg
        115                 120                 125
Ser Glu Lys Gly Pro Thr Thr Ser Phe Glu Ser Ala Ala Cys Pro Gly
    130                 135                 140
Trp Phe Leu Cys Thr Thr Leu Glu Ala Asp Arg Pro Val Ser Leu Thr
145                 150                 155                 160
Asn Thr Pro Glu Glu Pro Leu Ile Val Thr Lys Phe Tyr Phe Gln Glu
                165                 170                 175
Asp Gln
```

<210> SEQ ID NO 7
<211> LENGTH: 20
<212> TYPE: DNA
<213> ORGANISM: Mus musculus

<400> SEQUENCE: 7
gtatcagcaa cgtcaagcaa                                          20

<210> SEQ ID NO 8
<211> LENGTH: 20
<212> TYPE: DNA
<213> ORGANISM: Mus musculus

<400> SEQUENCE: 8
ctgcaggtca tcttcagtga                                          20

<210> SEQ ID NO 9
<211> LENGTH: 20
<212> TYPE: DNA
<213> ORGANISM: Mus musculus

-continued

<400> SEQUENCE: 9
tatcagcaac gtcaagcaac                                        20

<210> SEQ ID NO 10
<211> LENGTH: 20
<212> TYPE: DNA
<213> ORGANISM: Mus musculus

<400> SEQUENCE: 10
gccatagctt gcatcataga                                        20

<210> SEQ ID NO 11
<211> LENGTH: 20
<212> TYPE: DNA
<213> ORGANISM: Mus musculus

<400> SEQUENCE: 11
catcaacaag agcttcaggc                                        20

<210> SEQ ID NO 12
<211> LENGTH: 20
<212> TYPE: DNA
<213> ORGANISM: Mus musculus

<400> SEQUENCE: 12
tgctctcatc aggacagccc                                        20

<210> SEQ ID NO 13
<211> LENGTH: 20
<212> TYPE: DNA
<213> ORGANISM: Mus musculus

<400> SEQUENCE: 13
gctcatgtcc tcatcctgga                                        20

<210> SEQ ID NO 14
<211> LENGTH: 20
<212> TYPE: DNA
<213> ORGANISM: Mus musculus

<400> SEQUENCE: 14
cctcatcctg gaaggtccac                                        20

<210> SEQ ID NO 15
<211> LENGTH: 21
<212> TYPE: DNA
<213> ORGANISM: Mus musculus

<400> SEQUENCE: 15
ttactcctta ccttccagat c                                      21

<210> SEQ ID NO 16
<211> LENGTH: 21
<212> TYPE: DNA
<213> ORGANISM: Mus musculus

<400> SEQUENCE: 16
gaaactcagc cgtctcttct t                                      21

<210> SEQ ID NO 17
<211> LENGTH: 21
<212> TYPE: DNA

```
<213> ORGANISM: Mus musculus

<400> SEQUENCE: 17
caacttcacc ttcaaggaga g                                              21

<210> SEQ ID NO 18
<211> LENGTH: 21
<212> TYPE: DNA
<213> ORGANISM: Mus musculus

<400> SEQUENCE: 18
gtgtctttcc cgtggacctt c                                              21

<210> SEQ ID NO 19
<211> LENGTH: 21
<212> TYPE: DNA
<213> ORGANISM: Mus musculus

<400> SEQUENCE: 19
cacagcttct ccacagccac a                                              21

<210> SEQ ID NO 20
<211> LENGTH: 21
<212> TYPE: DNA
<213> ORGANISM: Mus musculus

<400> SEQUENCE: 20
gtgctgctgc gagatttgaa g                                              21

<210> SEQ ID NO 21
<211> LENGTH: 20
<212> TYPE: RNA
<213> ORGANISM: Mus musculus

<400> SEQUENCE: 21
guaucagcaa cgucaagcaa                                                20

<210> SEQ ID NO 22
<211> LENGTH: 20
<212> TYPE: RNA
<213> ORGANISM: Mus musculus

<400> SEQUENCE: 22
cugcagguca ucuucaguga                                                20

<210> SEQ ID NO 23
<211> LENGTH: 20
<212> TYPE: RNA
<213> ORGANISM: Mus musculus

<400> SEQUENCE: 23
uaucagcaac gucaagcaac                                                20

<210> SEQ ID NO 24
<211> LENGTH: 20
<212> TYPE: RNA
<213> ORGANISM: Mus musculus

<400> SEQUENCE: 24
gccauagcuu gcaucauaga                                                20

<210> SEQ ID NO 25
<211> LENGTH: 20
```

```
<212> TYPE: RNA
<213> ORGANISM: Mus musculus

<400> SEQUENCE: 25
caucaacaag agcuucaggc                                               20

<210> SEQ ID NO 26
<211> LENGTH: 20
<212> TYPE: RNA
<213> ORGANISM: Mus musculus

<400> SEQUENCE: 26
ugcucucauc aggacagccc                                               20

<210> SEQ ID NO 27
<211> LENGTH: 20
<212> TYPE: RNA
<213> ORGANISM: Mus musculus

<400> SEQUENCE: 27
gcucaugucc ucauccugga                                               20

<210> SEQ ID NO 28
<211> LENGTH: 20
<212> TYPE: RNA
<213> ORGANISM: Mus musculus

<400> SEQUENCE: 28
ccucauccug gaagguccac                                               20

<210> SEQ ID NO 29
<211> LENGTH: 21
<212> TYPE: RNA
<213> ORGANISM: Mus musculus

<400> SEQUENCE: 29
uuacuccuua ccuuccagau c                                             21

<210> SEQ ID NO 30
<211> LENGTH: 21
<212> TYPE: RNA
<213> ORGANISM: Mus musculus

<400> SEQUENCE: 30
gaaacucagc cgucucuucu u                                             21

<210> SEQ ID NO 31
<211> LENGTH: 21
<212> TYPE: RNA
<213> ORGANISM: Mus musculus

<400> SEQUENCE: 31
caacuucacc uucaaggaga g                                             21

<210> SEQ ID NO 32
<211> LENGTH: 21
<212> TYPE: RNA
<213> ORGANISM: Mus musculus

<400> SEQUENCE: 32
gugucuuucc cguggaccuu c                                             21

<210> SEQ ID NO 33
```

```
<211> LENGTH: 21
<212> TYPE: RNA
<213> ORGANISM: Mus musculus

<400> SEQUENCE: 33
cacagcuucu ccacagccac a                                               21

<210> SEQ ID NO 34
<211> LENGTH: 21
<212> TYPE: RNA
<213> ORGANISM: Mus musculus

<400> SEQUENCE: 34
gugcugcugc gagauuugaa g                                               21

<210> SEQ ID NO 35
<211> LENGTH: 81
<212> TYPE: RNA
<213> ORGANISM: Mus musculus

<400> SEQUENCE: 35
guuauaguac ucuggaaaca gaaucuacua aaacaaggca aaaugccgug uuuaucucgu      60
caacuuguug gcgagauuuu u                                               81

<210> SEQ ID NO 36
<211> LENGTH: 82
<212> TYPE: RNA
<213> ORGANISM: Mus musculus

<400> SEQUENCE: 36
guuauagagc uagaaauagc aaguuaaaau aaggcuaguc cguuaucaac uugaaaagu       60 ggcaccgagu cggugcuuuu uu                                              82
```